United States Patent
Qiu

(10) Patent No.: US 9,486,596 B2
(45) Date of Patent: *Nov. 8, 2016

(54) INTUBATION SYSTEMS AND METHODS BASED ON AIRWAY PATTERN IDENTIFICATION

(71) Applicant: Chunyuan Qiu, Huntington Beach, CA (US)

(72) Inventor: Chunyuan Qiu, Huntington Beach, CA (US)

(*) Notice: Subject to any disclaimer, the term of this patent is extended or adjusted under 35 U.S.C. 154(b) by 17 days.

This patent is subject to a terminal disclaimer.

(21) Appl. No.: 14/538,686

(22) Filed: Nov. 11, 2014

(65) Prior Publication Data

US 2015/0059736 A1  Mar. 5, 2015

Related U.S. Application Data

(63) Continuation of application No. 12/764,804, filed on Apr. 21, 2010, now Pat. No. 8,894,569.

(51) Int. Cl.
*A61M 16/04* (2006.01)
*A61M 16/00* (2006.01)
(Continued)

(52) U.S. Cl.
CPC ...... *A61M 16/0493* (2014.02); *A61B 1/00009* (2013.01); *A61B 1/015* (2013.01); *A61B 1/267* (2013.01); *A61M 16/0003* (2014.02);
(Continued)

(58) Field of Classification Search
CPC ............... A61M 16/0493; A61M 16/0003; A61M 16/0488; A61M 2205/50; A61M 2016/0015; A61M 2205/3327; A61M 2210/1032; A61M 2016/003; A61M 2205/3334; A61M 2016/0027; A61B 1/015; A61B 1/267; A61B 1/00009; A61B 1/0051; A61B 1/00135

USPC ............... 600/184–200; 128/200.26
See application file for complete search history.

(56) References Cited

U.S. PATENT DOCUMENTS 4,292,961 A  10/1981  Kawashima
4,366,810 A   1/1983  Slanetz, Jr.
(Continued)

FOREIGN PATENT DOCUMENTS

EP  0230790 A2  8/1987
WO  9934726 A1  7/1999
(Continued)

OTHER PUBLICATIONS

ISR United States Patent and Trademark Office, International Search Report of PCT/US2008/073176, WIPO, Nov. 14, 2008, 2 pages.
(Continued)

*Primary Examiner* — Christopher Beccia
(74) *Attorney, Agent, or Firm* — Alleman Hall McCoy Russell & Tuttle LLP

(57) ABSTRACT

An intubation system of the present disclosure intubates based on an airway pattern indicating a trachea opening. The airway pattern is determined from analysis of airway data detected by a trachea identifying device disposed on a moveable guide stylet of the intubation system. A navigation element is generated based on the airway pattern. In one embodiment, the airway pattern is a gas exchange pattern indicating a trachea opening. In another embodiment, the trachea opening transition pattern is a topographic pattern indicating a trachea opening. The guide stylet is capable of moving in a plurality of degrees of freedom in the airway following the guidance from the navigation element.

20 Claims, 7 Drawing Sheets

(51) Int. Cl.
*A61B 1/00* (2006.01)
*A61B 1/015* (2006.01)
*A61B 1/267* (2006.01)
*A61B 1/005* (2006.01)

(52) U.S. Cl.
CPC ......... *A61M16/0488* (2013.01); *A61B 1/0051* (2013.01); *A61B 1/00135* (2013.01); *A61M 2016/003* (2013.01); *A61M 2016/0015* (2013.01); *A61M 2016/0027* (2013.01); *A61M 2205/3327* (2013.01); *A61M 2205/3334* (2013.01); *A61M 2205/50* (2013.01); *A61M 2210/1032* (2013.01)

(56) References Cited

U.S. PATENT DOCUMENTS

| | | | |
|---|---|---|---|
| 4,437,458 A | 3/1984 | Upsher | |
| 4,469,091 A | 9/1984 | Slanetz, Jr. | |
| 5,095,888 A * | 3/1992 | Hawley | A61B 1/267 600/194 |
| 5,184,603 A | 2/1993 | Stone | |
| 5,257,636 A | 11/1993 | White | |
| 5,285,778 A | 2/1994 | Mackin | |
| 5,445,161 A | 8/1995 | Huang | |
| 5,492,131 A | 2/1996 | Galel | |
| 5,560,351 A | 10/1996 | Gravenstein et al. | |
| 5,591,130 A | 1/1997 | Denton | |
| 5,776,052 A | 7/1998 | Callahan | |
| 5,845,634 A | 12/1998 | Parker | |
| 5,951,461 A | 9/1999 | Nyo et al. | |
| 6,063,093 A | 5/2000 | Winston et al. | |
| 6,149,603 A | 11/2000 | Parker | |
| 6,161,537 A | 12/2000 | Gravenstein et al. | |
| 6,164,277 A | 12/2000 | Merideth | |
| 6,203,493 B1 | 3/2001 | Ben-Haim | |
| 6,349,720 B1 | 2/2002 | Clark | |
| 6,463,313 B1 | 10/2002 | Winston et al. | |
| 6,468,203 B2 | 10/2002 | Belson | |
| 6,659,962 B2 | 12/2003 | Ricciardelli | |
| 6,705,320 B1 | 3/2004 | Anderson | |
| 6,715,491 B2 | 4/2004 | Cooper et al. | |
| 6,757,557 B1 | 6/2004 | Bladen et al. | |
| 6,820,614 B2 | 11/2004 | Bonutti | |
| 6,858,005 B2 | 2/2005 | Ohline et al. | |
| 6,860,264 B2 * | 3/2005 | Christopher | A61M 16/04 600/120 |
| 6,869,396 B2 | 3/2005 | Belson | |
| 6,890,297 B2 | 5/2005 | Belson | |
| 6,926,709 B2 | 8/2005 | Bieger et al. | |
| 6,970,732 B2 | 11/2005 | Winston et al. | |
| 6,981,947 B2 | 1/2006 | Melker | |
| 7,044,907 B2 | 5/2006 | Belson | |
| 7,087,013 B2 | 8/2006 | Belson et al. | |
| 7,089,928 B2 | 8/2006 | Besharim et al. | |
| 7,153,260 B1 | 12/2006 | Girgis | |
| 7,174,202 B2 | 2/2007 | Bladen et al. | |
| 7,178,519 B2 | 2/2007 | Melker et al. | |
| 7,182,728 B2 | 2/2007 | Cubb et al. | |
| 7,194,296 B2 | 3/2007 | Frantz et al. | |
| 8,460,184 B2 * | 6/2013 | Nearman | A61B 1/267 600/188 |
| 8,652,033 B2 | 2/2014 | Berci et al. | |
| 2002/0074002 A1 | 6/2002 | Tung et al. | |
| 2002/0173799 A1 | 11/2002 | Besharim et al. | |
| 2003/0018276 A1 | 1/2003 | Mansy et al. | |
| 2003/0034035 A1 | 2/2003 | Raphael | |
| 2003/0092967 A1 | 5/2003 | Fourie et al. | |
| 2004/0039252 A1 | 2/2004 | Koch, III | |
| 2004/0199053 A1 | 10/2004 | Boulais et al. | |
| 2005/0076914 A1 | 4/2005 | Besharim et al. | |
| 2005/0107669 A1 | 5/2005 | Couvillon, Jr. | |
| 2005/0154261 A1 | 7/2005 | Ohline et al. | |
| 2005/0187434 A1 | 8/2005 | Dey et al. | |
| 2005/0209509 A1 | 9/2005 | Belson | |
| 2006/0004258 A1 | 1/2006 | Sun et al. | |
| 2006/0004260 A1 | 1/2006 | Boedeker et al. | |
| 2006/0122460 A1 | 6/2006 | Kamali | |
| 2006/0129055 A1 | 6/2006 | Orr et al. | |
| 2006/0180155 A1 | 8/2006 | Glassenberg et al. | |
| 2006/0201517 A1 | 9/2006 | Rich et al. | |
| 2007/0015967 A1 | 1/2007 | Boulais et al. | |
| 2007/0106117 A1 | 5/2007 | Yokota | |
| 2007/0106121 A1 | 5/2007 | Yokota et al. | |
| 2007/0106122 A1 | 5/2007 | Yokota et al. | |
| 2007/0129603 A1 | 6/2007 | Hirsh | |
| 2008/0236575 A1 * | 10/2008 | Chuda | A61B 1/00052 128/200.26 |
| 2009/0044799 A1 | 2/2009 | Qiu | |
| 2013/0035548 A1 * | 2/2013 | Ianchulev | A61B 1/06 600/120 |

FOREIGN PATENT DOCUMENTS

| | | |
|---|---|---|
| WO | 04000107 A2 | 12/2003 |
| WO | 2009023779 A1 | 2/2009 |

OTHER PUBLICATIONS

"Karl Storz Endoscopy-America, Inc." <http://www.anesthesiologynews.com/ancp/0808/content/ancp0808_042a.html?pagename=karl_storz_corporate_profile>, 2 pages, Accessed Dec. 4, 2009, 2 pages.

Wagner, Jason. "The Storz Video Laryngoscope." <http://www.epmonthly.com/subspecialties/technology/the-storz-video-laryngoscope/>, 3 pages, Accessed Dec. 4, 2009, 3 pages.

* cited by examiner

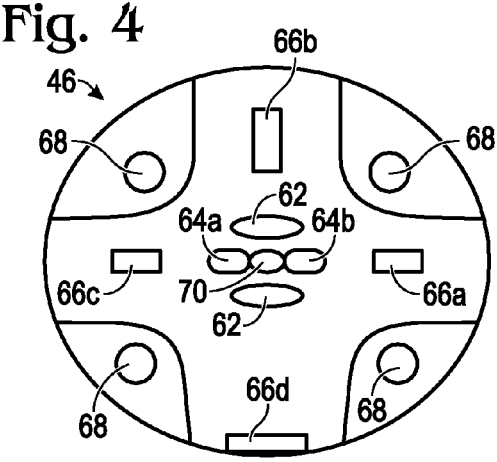
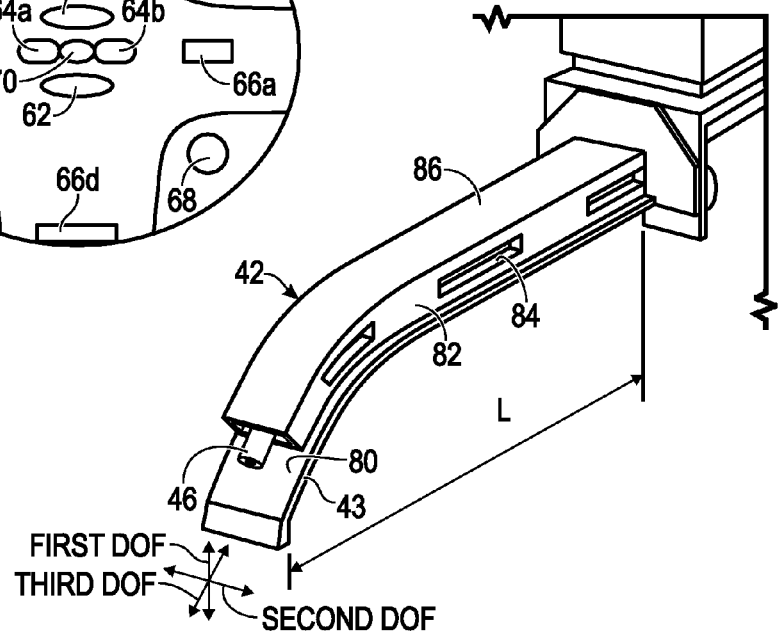
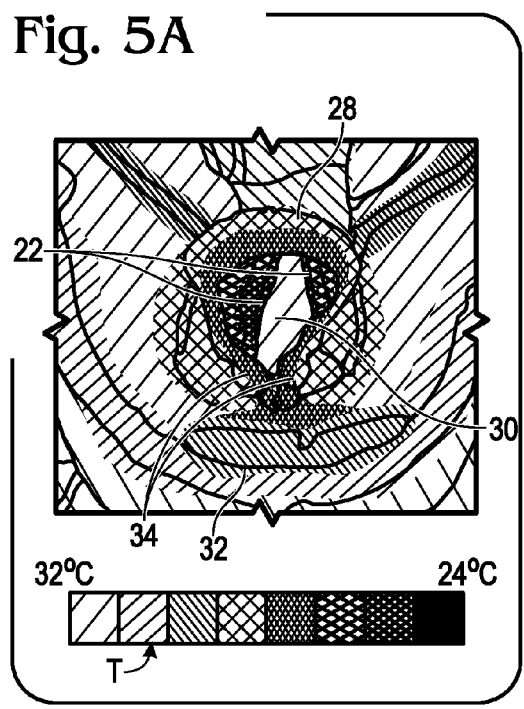
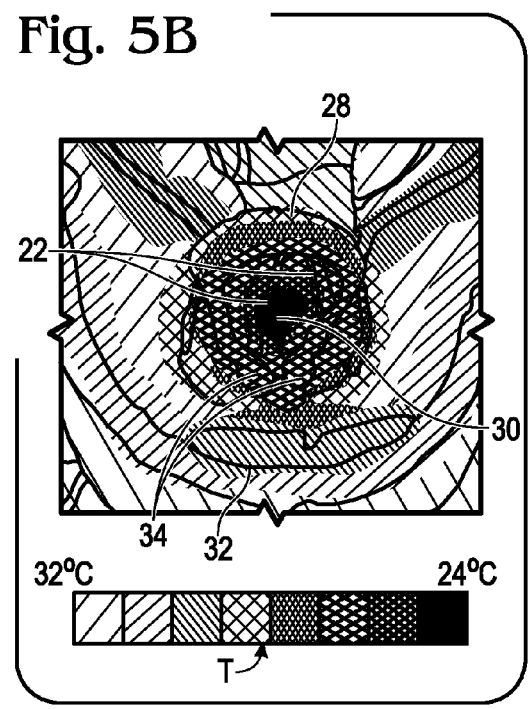

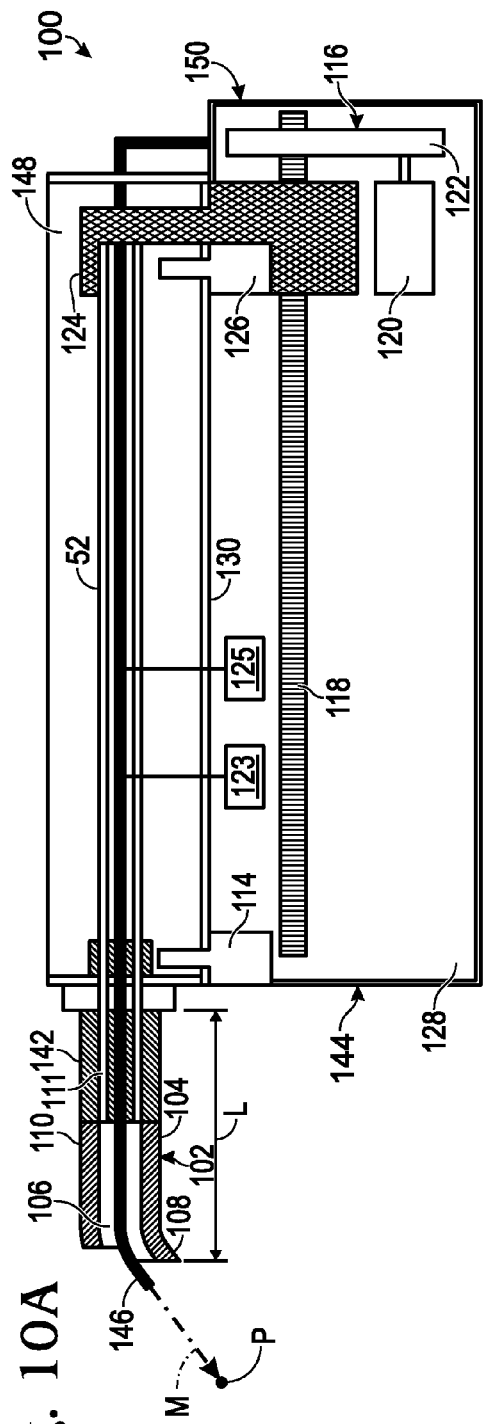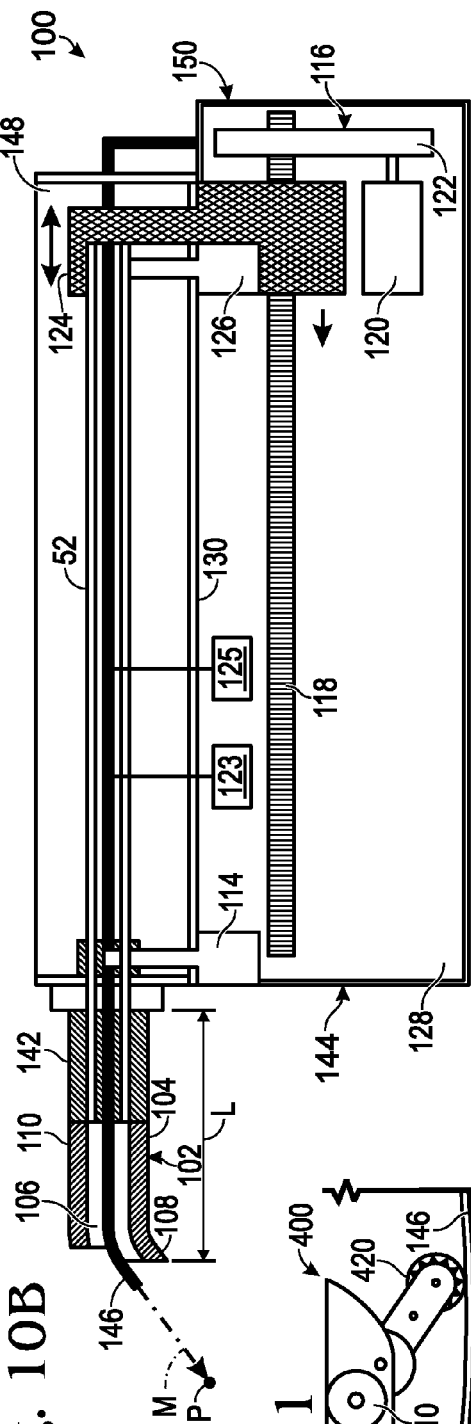

INTUBATION SYSTEMS AND METHODS BASED ON AIRWAY PATTERN IDENTIFICATION

CROSS-REFERENCE TO RELATED APPLICATIONS

The present application is a continuation of U.S. patent application Ser. No. 12/764,804, entitled "INTUBATION SYSTEMS AND METHODS BASED ON AIRWAY PATTERN IDENTIFICATION," filed on Apr. 21, 2010, the entire contents of which are hereby incorporated by reference for all purposes.

TECHNICAL FIELD

The present disclosure relates generally to systems and methods to intubate a patient, and more particularly to systems and methods to intubate a patient based on dynamic airway-specific patterns indicating a trachea opening.

BACKGROUND

Some medical procedures are invasive and potentially dangerous although they are necessary life-saving procedures. Intubation, specifically tracheal intubation, is typically performed at various medical conditions, such as application of general anesthesia, comatose, etc. Tracheal intubation involves the placement or the insertion of an endotracheal tube (ETT) into a patient's trachea via the vocal cords to protect the patient's airway and provide a mechanism to enable ventilation. Delay and/or misplacement of the ETT, such as misplacement of the ETT into the esophagus, may cause permanent neurological damage or death. Malposition of the ETT also may jeopardize airway protection or cause inadequate ventilation. It is therefore imperative to intubate a patient quickly and position the ETT correctly when a medical condition arises.

Various technologies have been developed to assist the placement of the ETT into the trachea. In a laryngoscope technique, a laryngoscope is used to obtain a direct view of the glottis and the ETT is then inserted into the trachea under direct vision or indirect vision. A laryngoscope typically includes a blade that has various shapes and lengths and is made of rigid materials. In a direct laryngoscope, a light source is coupled to the guide blade to assist the view of the glottis. In a video laryngoscope, a video camera along with a light source is positioned on the guide blade to provide a video image to guide the insertion of the ETT. When intubating a patient with the laryngoscope technique, a user typically inserts the guide blade into a patient's mouth with one hand, and inserts the ETT into the trachea with another hand once the trachea is identified. Successful intubation is defined as a successful ETT insertion into the patient's trachea.

Intubation may not be successful due to various reasons. Failed intubation with a direct laryngoscope may occur due to poor visualization and identification of the glottis or vocal cords, a situation called "can't see and can't intubate." Failed intubation with a video laryngoscope may occur due to a poor visualization or poor angle for the ETT insertion as a result of indirect video image of the vocal cords. A situation called "can see but can't intubate" is common. Further, all current intubation is performed by two hands (i.e., one hand holding the guide blade and another hand inserting the ETT), the ETT may not be inserted correctly due to poor visual-hand coordination during the insertion of the ETT. Furthermore, there are clinical situations that can make both visualization of the vocal cords and correct identification impossible with either direct laryngoscope or video laryngoscope, such as intubation for the patients with a limited mouth opening, short or limited neck motion or neck pathologies, pregnancy and obesity, etc.

SUMMARY

The inventor herein has recognized that the above issues may be addressed by an intubation system that identifies a trachea opening through airway pattern identification. In one aspect, an intubation system comprises a moveable guide stylet to be inserted into an upper airway of a patient to guide insertion of an endotracheal tube into a patient's trachea; at least one trachea identifying device positioned on the guide stylet to detect airway data as the guide stylet moves in the upper airway; and an insertion guide device including a data processor configured to analyze the airway data to determine an airway pattern indicating a position of the guide stylet relative to a trachea opening, and generate a navigation element to direct a movement of the guide stylet to the trachea opening. In one embodiment, the airway pattern is a topographical pattern. In another embodiment, the airway pattern is a gas exchange pattern. In yet another embodiment, the airway pattern is a sound pattern. The airway pattern indicating a position of the guide stylet relative to a trachea opening may be determined via pattern matching or pattern recognition.

The pattern matching and the pattern recognition may enable identification of the topographic features that cannot be observed by human eyes or cannot be identified correctly by human eyes via a direct video image under some clinical conditions. Further, the intubation system may identify one or more topographical features and select the identifiable topographical features to determine the topographical pattern indicating the trachea opening. Trachea identification based on analysis of selected topographical features allows the trachea identification under some clinical conditions where some topographical features are not identifiable due to abnormality or trauma of the epiglottis, the vocal cords, etc. In this way, the intubation system allows accurate and fast identification of the trachea and increases the success rate of the intubation in various clinical situations.

The gas exchange pattern indicating the trachea opening makes it possible to intubate the patient without relying on the visualization of the glottis or vocal cords. The pattern matching or pattern recognition based on a large number of data increases the accuracy of the trachea identification. Further, computerized data analysis can shorten the time for the trachea identification as compared to the trachea identification based on the human judgment.

The intubation system of the present disclosure identifies a trachea opening such that the guide stylet can be directed to an entrance to the trachea. In this way, the trachea location can be identified and differentiated from the esophagus opening to ensure correct insertion of the guide stylet into the trachea.

According to yet another aspect, the intubation system comprise a blade including a distal end, the distal end adjacent to a trachea opening when the blade is inserted into an upper airway of a patient; a guide stylet disposed in the blade and moveable along the blade to guide insertion of an endotracheal tube into a patient's trachea; at least one trachea identifying device positioned on the guide stylet to detect airway data as the guide stylet moves in the upper airway; and an insertion guide device including a data processor configured to analyze the airway data to determine an airway pattern indicating a position of the guide stylet relative the trachea opening, and generate a navigation element to direct a movement of the guide stylet to the trachea opening, a display device to display the navigation element, a drive mechanism to move the guide stylet at three degrees of freedom, and an actuator configured to actuate the drive mechanism via a user of the intubation system.

As the guide stylet performs movement in at multiple degrees of freedom, the guide stylet's movement can be adjusted easily in response to the navigation guidance to enable a quick search for the trachea. The blade configuration can assist the guide stylet's movement in multiple degrees of freedom. Further, because the intubation system is configured to enable the ETT to move along the guide stylet, the ETT follows exactly the same path of the guide stylet to the trachea or the ETT is in-line with the guide stylet. Thus, the intubation system can solve the problems of uncommon angulation for the ETT insertion. Further, the errors associated with coordinating the ETT insertion with two hands can be reduced or eliminated.

The in-line alignment of the ETT and the guide stylet according to the present disclosure can be performed manually, or via a motor drive mechanism semi-automatically or automatically. In this way, the intubation can be done easily. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 4 is an exploded front or cross-sectional view of an example guide stylet of an intubation system according to one embodiment of the present disclosure.

FIGS. 5A and 5B show thermal images, schematically illustrating a topographical pattern indicating the trachea opening, an esophagus opening, and their surroundings.

FIG. 8 shows an example embodiment of blade and guide stylet of an intubation system according to the present disclosure.

FIGS. 10A and 10B shows a cross section view of an intubation system according to another embodiment of the present disclosure.

FIG. 11 shows an example drive mechanism for one degree of freedom of movement of an intubation system according to another embodiment of the present disclosure.

DETAILED DESCRIPTION

Figure 1:
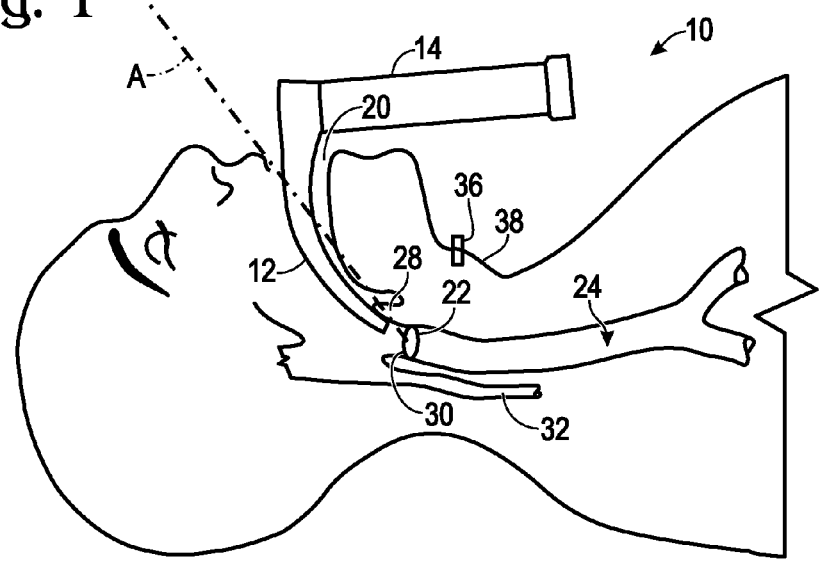
FIG. 1 shows a schematic view of an intubation device as used to intubate a patient.

As described in more detail below, in some embodiments, an intubation system of the present disclosure intubates a patient based on an airway-specific pattern from airway data generated from an airway sensor disposed on a guide stylet. The airway of a human being comprises system of conduits, i.e., conducting airway. The airway comprises an upper airway system or an upper airway and a lower airway system or a lower airway. The upper airway and the lower airway are divided by a trachea opening. The trachea opening is an opening defined by the vocal cords or a glottis opening. Intubation is a process to navigate an ETT from the upper airway through the trachea opening (e.g., the vocal cords, the glottis opening) into the lower airway.

When the guide stylet is inserted into an upper airway of a patient, the airway sensor detects the airway data related to the characteristics of the airway, such as a trachea opening. In one example, the airway data are topographical data associated with the anatomical features of the trachea opening. In another example, the airway data are gas exchange data associated with the gas exchange in the airway. In yet another example, the airway data are sound level associated with sound generated by the vocal cords in the airway. The airway data are analyzed to determine an airway pattern indicating a position of the guide stylet relative to a trachea opening. A navigation element is generated based on the airway pattern. For example, when the airway pattern indicates that guide stylet is positioned away from the trachea opening or at a location in front of the esophagus opening or adjacent esophagus opening, the navigation element is generated to indicate whether the guide stylet is at the trachea opening. In one example, the navigation element may be a display, such as "the guide stylet is not at the trachea opening" or "trachea is not found." In another example, as the trachea opening is located in front of the esophagus opening in an insertion direction and is above the esophagus opening relative to the insertion direction, the navigation element may be generated to provide instructions for the guide stylet's movement according to the spatial location of the trachea opening and the esophagus opening. For example, the navigation element may indicate a relative position of the trachea opening and/or provide a direction for the guide stylet's movement as the guide stylet moves in the upper airway, such as "trachea is upward, move upward and forward" based on the airway pattern. Likewise, when the airway pattern indicates that guide stylet is positioned adjacent to the trachea opening and in front of the trachea opening, the navigation element may be a display, such as "the guide stylet is at the trachea opening" or "trachea is found."

As described in detail below, in one embodiment, the airway sensor is an image capture device and the airway pattern is a topographical pattern indicating a position of the guide stylet relative to a trachea opening. In another embodiment, the airway sensor is a gas exchange detector and the airway pattern is a gas exchange pattern indicating a position of the guide stylet relative to a trachea opening. In yet another embodiment, the airway sensor is a sound detector and the airway pattern is a sound pattern indicating a position of the guide stylet relative to a trachea opening. In some embodiments, the airway pattern indicating a trachea may be identified via pattern matching techniques or pattern recognition techniques.

In some embodiments, the airway pattern may an airway pattern in front of the trachea opening and adjacent to the trachea opening. In one example, the airway pattern is a topographic pattern in front and adjacent to the trachea opening, where the topographic pattern presents the topographical features of the trachea opening, such as distinctive features of the vocal cords and other features surrounding the vocal cords. In another example, the airway pattern is a gas exchange pattern in front and adjacent to the trachea opening or the gas exchange pattern in the trachea, where the gas exchange pattern presents gas exchange features adjacent the trachea opening or the gas exchange features in the trachea. In still another example, the airway pattern is a sound pattern at the trachea opening (i.e., the vocal cords) or the sound pattern in the trachea, wherein the sound pattern is recognizable.

FIG. 1 shows a schematic view of an intubation device 10 as used to intubate a patient. Intubation device 10 includes a blade 12 and a laryngoscope 14 configured to provide a view of an epiglottis and vocal cords. Blade 12 is adapted to be inserted into a patient's trachea 24 via an upper airway of a patient, i.e., via a patient's mouth 20 and vocal cords 22. FIG. 1 also illustrates possible paths during the blade placement. As shown in FIG. 1, epiglottis 28 and glottis 30 are in the front of vocal cords 22. Esophagus 32 is under trachea 24. Trachea 24 is located anterior to esophagus 32. Two cavities, trachea 24 and esophagus 32, are adjacent each other. Thus, blade 12 may be inserted into either trachea 24 or esophagus 32. Positioning of the ETT into the esophagus results in failure of the intubation and may jeopardize airway protection or cause inadequate ventilation.

FIG. 1 shows that blade 12 is inserted into the mouth and a blade tip is positioned in front of the trachea opening along a line A. When it is determined that blade 12 is at the opening of trachea 24, the ETT (not shown) is pushed into trachea 24. Once the ETT is in the trachea, blade 12 is removed from trachea 24 and the intubation is completed. The ETT tube remains in trachea 24 for a period as required for the medical procedure.

Figure 2:
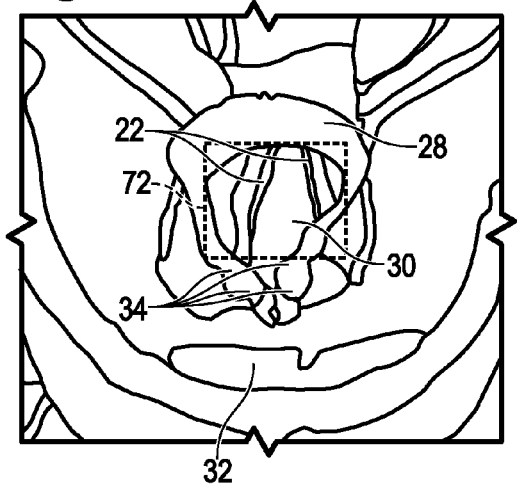
FIG. 2 shows a view of a trachea opening, an esophagus opening, and their surroundings.

FIG. 2 shows a view of a trachea opening, an esophagus opening and their surroundings. Trachea is an open tube-like cartilage structure with vocal cords as its opening while esophagus 32 is a muscle and connective tissue structure collapsed in the absence of swallowing. The shape of the trachea opening or the vocal cords is substantially different from the shape of the esophagus opening in the size, and the anatomical relationship to epiglottis 28, glottis 30 and arytenoids cartilages 34. As such, the structural features constitute topographical features that distinguish the trachea opening from the esophagus opening.

Further, vocal cords 22 at the trachea opening possess specific features. As shown in FIG. 2, vocal cords 22 consist of twin infoldings of mucous membrane stretched horizontally across the larynx and open in an inverse V-shape. Unlike its surrounding structures, vocal cords 22 are white-colored, which constitutes another identifiable feature. Additionally, while the vocal cords or folds typically remain still at rest, the vocal folds vibrate during phonation and thus create an additional identifiable feature. Furthermore, the vocal cord is a narrowest part that divides the upper airway and a lower airway, which possess characteristics or a specific air flow pattern that differentiates the vocal cord from the other structures of the upper airway and from the esophagus opening. The variations of the dimension of the vocal cords opening and the vocal cords' motion create additional identifiable features.

Further, additional topographical features include, but are not limited to, the spatial relationship, relative position, relative color of the epiglottis, the arytenoids cartilages, the vocal cords, the trachea opening, and the esophagus opening.

One or more of the topographic features described above form a topographical pattern. The topographical pattern indicating the trachea opening can be identified from the image data captured by an image capture device. In other words, one or more of the topographic features can be used as biometrics for the trachea identification via any appropriate data analysis techniques.

In addition to the topographic pattern indicating the trachea opening, a gas exchange pattern of the trachea can be used for the trachea identification as described in detail below. Furthermore, a sound pattern can be used for the trachea identification as described in detail below.

Figure 3:
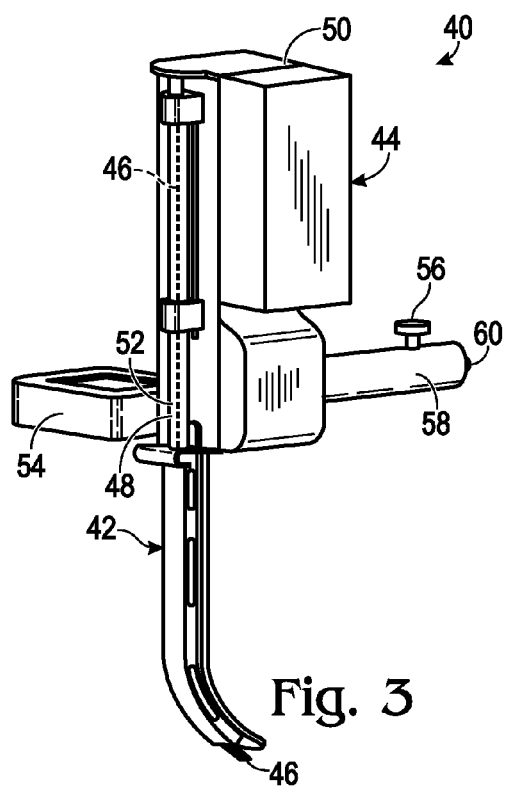
FIG. 3 illustrates an example embodiment of an intubation system according to the present disclosure.

FIG. 3 illustrates an example embodiment of an intubation system 40 according to the present disclosure. Intubation system 40 typically includes a guide blade or a blade 42 and an insertion guide device 44. A guide stylet 46 is disposed in the blade 42. In some embodiments, guide stylet 46 may be configured to be positioned in a center of blade 42 along a blade's length and connected with insertion guide device 44 electronically and mechanically. An endotracheal tube compartment 48 may be included in an insertion guide device enclosure 50 such that an ETT 52 can be preloaded thereof. In the depicted embodiment, ETT 52 is positioned in such way that a longitudinal axis of ETT 52 is substantially concentric with a longitudinal axis of guide stylet 46. In this way, ETT 52 can be slipped over guide stylet 46 and pushed in with the same moving path as that of guide stylet 46. Alternatively, the longitudinal axis of ETT 52 may not be overlapped with the longitudinal axis of guide stylet 46. ETT 52 is positioned side-by side with guide stylet 46 as ETT 52 is pushed into blade 42. The ETT's movement can be guided by guide stylet or a blade body during the ETT insertion.

Insertion guide device 44 may include a mechanism for identifying the trachea and directing the insertion of ETT 52. The trachea may be identified with a trachea identifying device or by analyzing data detected by a trachea identifying device. The trachea identifying device may be disposed on a tip portion of the guide stylet to detect various data that can be used to identify the trachea as described in detail below. In some embodiments, insertion guide device 44 may include a data processor configured to receive the data detected by a trachea identifying device, analyze a pattern of the detected data and generate a navigation element to direct the guide stylet's movement. The navigation element may be a navigation guidance display generated by software or hardware of the intubation system. Alternatively, the navigation element may be a directional movement generated by the software, hardware or a controller to enable semi-automatic or automatic movement of the guide stylet.

The navigation element indicates whether the guide style is in the trachea opening or in the trachea as the guide stylet is moving in the airway. When the navigation element indicates that the guide stylet is in the trachea opening, ETT 52 can be moved in the airway following the guide stylet' path. Once ETT 52 is inserted into the trachea, the guide stylet is withdrawn and the intubation is completed.

Additionally, or alternatively, intubation system may include a display device 54 to display the navigation element. For example, display device 54 may display the navigator to direct the guide stylet's movement, such as "trachea not found" or "trachea found" as the guide stylet moves in the airway. The guide stylet's movement can be adjusted based on the navigation element. Further, display device 54 may present the detected real time data or the airway pattern as the navigation element. In the depicted embodiment, display device 54 is a separate component and is positioned adjacent to blade 42. It should be appreciated that display device 54 may be disposed on any positions suitable for an operation of an intubation system. Display device 54 may be connected to insertion guide device 44 via wire connection or wireless connection. In some embodiments, display device 54 may be a display screen remotely located from insertion guide device 44. Alternatively, display device 54 may be integrated into insertion guide device enclosure 50.

Intubation system 40 may also include a drive mechanism to drive or move guide stylet 46. The drive mechanism may cause the guide stylet's to move in one degree of freedom or multiple degrees of freedom such that the guide stylet can be moved in any desired directions for locating the trachea. In some embodiments, an actuator 56 may be used to operate the intubation system semi-automatically by a user. For example, the actuator 56 may be a joystick that is controlled by the user to move guide stylet 46 in any desired directions based on the navigation element presented in display device 54.

Intubation system 40 may further include a controller to drive the guide stylet automatically. The controller may be configured to receive the data detected by the trachea identifying device, analyze a pattern or patterns of the detected data, generate a navigation element, and adjust the movement of the guide stylet by the drive mechanism based on the navigation element. In some embodiments, actuator 56 may be configured to initiate the automatic insertion of the guide stylet and override the automatic intubation if necessary.

Additionally, or alternatively, intubation system 40 may include a lock/release device 58, such as a solenoid to couple guide stylet 46 and/or ETT 52 during the intubation as described in detail below.

Further, intubation system 40 may include a power supply 60 that provides power required by the electronic and/or mechanical components of the intubation system. In some embodiments, power may be supplied from an external power source, such as an AC outlet or external power source or combination of the two power sources. Alternatively, power supply 60 may include one or more batteries in a battery compartment of power supply 60.

FIG. 4 is an exploded front or cross-sectional view of an example guide stylet 46 of an intubation system according to one embodiment of the present disclosure. FIG. 4 illustrates the example trachea identifying devices disposed on a tip portion of the guide stylet. The trachea identifying devices are used to identify or locate a trachea or a trachea opening with any appropriate mechanisms. The trachea identifying devices may also be referred as the trachea opening identifying devices. The trachea identifying devices include, but not limited to a light source, an image capture device, a gas exchange detector, a sound detector, and a light detector as described in detail below. It should be appreciated that one trachea identifying device can be used alone in an intubation system for the trachea identification, or a combination of two or more trachea identifying devices can be used in an intubation system for the trachea identification.

Guide stylet 46 may include one or more of light sources 62. Light sources 62 may include a light-emitting diode (LED) or fiber optics. Light sources 62 provide illumination in front of the guide stylet to enable viewing of a trachea opening and its surroundings by a user of the intubation system or provides illumination for an image capture device 64 disposed on the guide stylet. In some embodiments, light sources 62 operate to indicate the trachea opening. For example, a user can identify the trachea opening through a direct view of the glottis or vocal cords under the light provided by light sources 62.

In some embodiments, one or more image capture devices 64$a$ and 64$b$ or image sensors may be disposed on guide stylet 46. The image capture device may be a video camera to continually capture images or a still camera to capture still images. In another example, the image capture device may be a thermal camera or an infrared camera to capture thermal images. Thermal images are generated based on the temperature difference of captured objects. It should be appreciated that the intubation system may include one or more types of cameras. Further, the intubation system may include two or more cameras of the same type and positioned in different locations of guide stylet 46. For example, two or three video cameras may generate two or three-dimensional image. The three dimensional images may identify the topographic features that cannot be identified by a two-dimensional image.

In some embodiments, the trachea identifying devices disposed on the blade may include one or more gas exchange detectors 66$a$, 66$b$, 66$c$, and 66$d$ to detect dynamic gas exchange data during a respiratory cycle. The gas exchange data may include temperature, air flow rate, positive or negative pressure, concentrations of carbon dioxide ($CO_2$), oxygen, or nitrogen. In one example, the gas exchange detectors may be a temperature sensor, an airflow sensor, a pressure sensor, a $CO_2$ sensor, an oxygen sensor, a nitrogen sensor, or a humidity sensor. It should be appreciated that one type of gas exchange detector may be used in the intubation system or two or more of different types of gas exchange detector may be used in the intubation system. Further, it should be appreciated that the gas exchange detector may be any suitable sensors that can detect the variables, such $CO_2$, oxygen and nitrogen, flowrate or pressure qualitatively or quantitatively with an appropriate response time to the concentration changes. Further, one gas exchange detector can be used in combination with one image capture device. In one embodiment, a $CO_2$ sensor may used to confirm the trachea location after the trachea is identified by the image data.

It should be appreciated that the trachea identifying device may include any device that can distinguish the trachea from the esophagus. In one example, the trachea identifying device may be a sound detector or a sound homing device. The sound homing device may include an arrangement of a plurality of microphones in the guide stylet to record sounds from different locations to detect vocal cord location. The trachea may be identified when sound in a predetermined decibel level is detected. In another example, the trachea identifying device may be a sound detector to detect sound in the trachea generated by phonation, or special phonation or sound, such as "Ah or Oh." The sound features may include decibel level of the sound. The sound pattern or sound recognition may be determined by any techniques known in the art.

Additionally, in some embodiments, the trachea identifying devices may be one or more detector that can sense a compound or a tracer introduced into the patient's gas exchange by inhalation, digestion or injection. For example, the compounds may include intravenous alcohol, helium, inhalation anesthetics (e.g., desflurane, isoflurane, sevoflurane), Xenon, or nitrous oxide ($N_2O$), etc. Detection of the introduced compound can indicate the trachea location.

Additionally, in some embodiments, the trachea identifying devices may be one or more signal sensors that can sense a signal generated by a signal generator attached to the patient. Referring back to FIG. 1, a signal generator 36 may be disposed on a patient's neck. In one example, signal generator 36 may be a light source configured to generate any suitable light, such as visible light, ultraviolet, infrared, laser, etc. In another example, signal generator 36 may be a sound device configured to create and send sound, such as audible sound or ultrasound in any suitable decibel level to trachea 24. Thus, the signal sensor may be a light sensor or a sound sensor capable of detecting the introduced light or sound. It should be appreciated that signal generator 36 may be disposed on the patient's neck 38 above trachea 24 as shown in FIG. 1 or signal generator 36 may be disposed inside the patient body and adjacent to trachea 24. The intubation system allows the trachea identification based on the introduced signal in some conditions, such as un-breathing patient, or abnormal airway.

Returning to FIG. 4, additionally, or alternatively, direction control cables 68 may be coupled to blade 42. As described below, in some embodiments, direction control cables 68 may be used to adjust the movement of guide stylet 46 in any desired direction by a drive mechanism for semi-automatic or automatic intubation.

Additionally, or alternatively, a precision light guide 70 may be disposed on guide stylet 46 to direct the insertion of the ETT. In one example, precision light guide 70 may be a laser pointer or other light pointers to generate a straight light ray that point toward a direction of an ETT pathway. Precision light guide 70 may be positioned adjacent to the trachea identifying device in an orientation such that the light path of precision light guide 70 is aligned with a moving path of the trachea identifying device. In this way, the light ray from alignment aid is directed to the trachea opening when the trachea is identified. As such, the ETT can follow the light ray when the ETT is pushed into the airway.

As described above, insertion guide device 44 may include one or more mechanisms for the trachea identification. In some embodiments, a data processor of insertion guide device 44 may be configured to receive the data detected by a trachea identifying device, analyze a pattern of the detected data and generate a navigation guidance based on the pattern. For example, the trachea identifying device may be an image capture device and the pattern may be a topographical pattern. Referring back to FIG. 2, an image captured by a video camera or a still camera may be displayed in display device 52 as shown in FIG. 2. As the camera moves in the airway, the images are captured continually or periodically and the real time image data are analyzed for the topographical pattern indicating a trachea opening.

The image data may be analyzed for the presence of the topographical features. As described above, the topographical features include the configuration of the vocal cords, such as an inverted "V" shape at rest, distinguished white color, vibrated folds of the vocal cords at phonation and the dynamic thermal image changes during a respiratory cycle. The topographical features further include structures surrounding the vocal cords, such as the shape of the epiglottis and arytenoids cartilages, and the esophagus opening as well as the vocal cords' spatial relationship and the vocal cords' relative color to its surrounding structures. In some embodiments, the topographical features of the vocal cords may be used alone to identify the vocal cords or the trachea opening. In other embodiments, the topographical features of the vocal cords may be used as a major identifier, and other topographical features surrounding the vocal cords and their relationship may be used as additional identifiers to confirm the trachea opening identification.

The topographical pattern indicating the trachea opening may be identified using any appropriate data processing technologies that identify a pattern based on the specific features. In one embodiment, the image data may be analyzed using pattern matching that checks for the presence of the constituents or features of a given pattern. For example, the image data may be analyzed for the presence of the topographic features by comparing a predetermined pattern. The predetermined pattern may be a specific topographic pattern for adults or a specific topographic pattern for children. Additionally, the pattern matching may include a comparison with a predetermined pattern for patients with an abnormal airway.

Pattern matching may include checking the presence of one or more of the topographical features in the captured data. In one example, it may be determined that the topographical pattern indicating the trachea opening is present if the captured image data include features matching the structural features of the vocal cords and/or epiglottis. In another example, it may be determined that the topographical pattern indicating the trachea opening is present if the captured image data include features matching the features of the vocal cord folds vibration or the motion in the trachea opening during phonation. Based on the analysis of the topographical pattern, the navigation guidance may be generated to direct the movement of the guide stylet. It should be appreciated that the navigation guidance may be generated if any single topographical feature matches with the predetermined pattern or if two or more topographical features match with the predetermined pattern. Further, it should be appreciated that any appropriate mathematic models can be used for pattern matching.

The pattern matching may enable identification of the topographic features that cannot be observed by human eyes or cannot be identified correctly by human eyes via a direct video image under some clinical conditions. Further, the trachea identification based on analysis of selected topographical features allows the trachea identification under some clinical conditions where it is difficult to identify some topographical features due to abnormality or trauma of the epiglottis, the vocal cords, etc. Further, the pattern matching has the advantage of selecting a predetermined pattern to be adapted to different groups of patients.

In some embodiments, the image data may be analyzed using pattern recognition based on the categories of the pattern. The pattern recognition technique may include collecting data, extracting features (e.g., numeric or symbolic information from the data) from the collected data and classing/categorizing the data based on the extracted features. Any appropriate pattern recognition technique can be used for the pattern recognition. In one example, the pattern recognition may be based on a prior knowledge via supervised learning. That is, the classification may be based on a set of classified or described patterns called the training set. In another example, the pattern recognition may establish the classes based on statistical regularities of the pattern, i.e., unsupervised learning. The data processor of the present disclosure may store one or more sets of classified patterns with the topographic features and perform the pattern recognition via the supervised learning. Alternatively or additionally, the data processor of the present disclosure may perform the pattern recognition based on a statistical model of the topographic features via unsupervised learning. Again, the topographic features may be one or more of the topographic features of the trachea, the esophagus and their surrounding, and the trachea identification may be based on recognition of one or more of the topographic features. The navigation guidance may be generated based on the pattern recognition. It should be appreciated that any appropriate mathematic models or algorithms can be used for pattern recognition.

In some embodiments, the data processor may further include locking the trachea opening once the trachea is found by a technique called targeting and locking. Referring back to FIG. 2, the image shown in FIG. 2 may be captured by the image capture device and displayed on a display device. A block 72 may appear in the image and block 72 follows the trachea opening as the guide stylet moves in the airway. In this way, the guide stylet's movement can be adjusted following block 72 and compensating the involuntering movement of the operator or patient.

In some embodiments, a controller or the data processor may include a position tracking module to track a position of the guide stylet via an image corresponding to the position. In one example, the position tracking module may include a predetermined map with a relationship between the airway images and positions of the guide stylet. As such, during the intubation, a current position of the guide stylet relative to the trachea opening (e.g., up, down, right or left relative to the trachea opening) may be determined by comparing the captured image with the predetermined map. Further, the position of the guide stylet and the real time movement of the guide stylet may be displayed on the display device along with the navigation element. The navigation element may further provide instructions indicating the location of the trachea opening, such as up, down, right or left relative to the current position of the guide stylet.

Again, as pattern recognition is conducted on a significant amount of real time data for the regularities or classification, pattern recognition may enable identification of the topographic features that cannot be observed by human eyes. The features identifiable by the pattern recognition are referred to as the machine recognizable features. Further, the identification of one or more machine recognizable features as opposed to the observation on an overall visualization of an image allows the correct trachea identification under the clinical conditions where an intubation is not possible by a direct view or a video image.

It should be appreciated that any suitable data processing may be used to analyze the topographical pattern indicating the trachea opening. For example, the data processor may include an image reconstruction module or an algorithm to recreate an image based on the captured image data. For example, an undiscernible topographical feature from a captured video image may be enhanced on a processed image once the feature is identified by the image reconstruction module. Alternatively, a missing topographical feature in the captured image may be superimposed into the processed image so that the trachea opening can be identified. The processed image can be displayed to a user. The processed image can improve the visualization of the trachea opening. In one example, the processed image alone can be displayed and used as the navigation element.

Further, the captured images may be used to identify the trachea without additional data processing. In some embodiments, the trachea identifying device may be a thermal camera or an infrared camera to capture the thermal images. FIGS. 5A and 5B show thermal images, schematically illustrating a topographical pattern indicating the trachea opening, an esophagus opening, and their surroundings. The temperatures in the trachea and esophagus are different. The temperature variation can be captured by the thermal camera. The thermal image may show the different temperature regions in different colors. In the depicted embodiment, a lighter shade represents a higher temperature while a darker shade represents a lower temperature as shown in a temperature bar T. In one example, the inverse V shape shown in the thermal image can be used to identify the vocal cords, and thus identify the trachea. In another example, temperature variations of glottis 30 or a vocal cord opening during a respiratory cycle can be used to identify the trachea as the thermal images changes during the respiratory cycle. For example, air flowing into the airway may be at the ambient temperature (e.g., room temperature of 24° C.) and the air flowing out of the trachea may at temperature of up to 32° C. FIG. 5A shows an example thermal image during the exhalation. As the exhaled gas has higher temperature, glottis is shown to have a lighter color. FIG. 5B shows an example thermal image during the inhalation. As the inhaled gas has lower temperature, the vocal cord opening or glottis 30 is shown to have a darker color. The color of glottis 30 shows significant changes in the respiratory cycle. In other words, the topographical features may include the thermal image color variations of the vocal cords and a vocal cord opening due to temperature changes in a respiratory cycle of the patient.

Further, the extent of the temperature difference can be further amplified by lowering the temperature of the inhaled air. As such, it can be determined the topographical pattern indicating the trachea opening once the significant color change of glottis are observed during the respiratory cycle. In this way, the images captured by the thermal camera can be use as the navigation guidance without additional data analysis, such as pattern matching or pattern recognition. Alternatively, additional data analysis, such as pattern matching or pattern recognition may be also used.

Figure 6A:
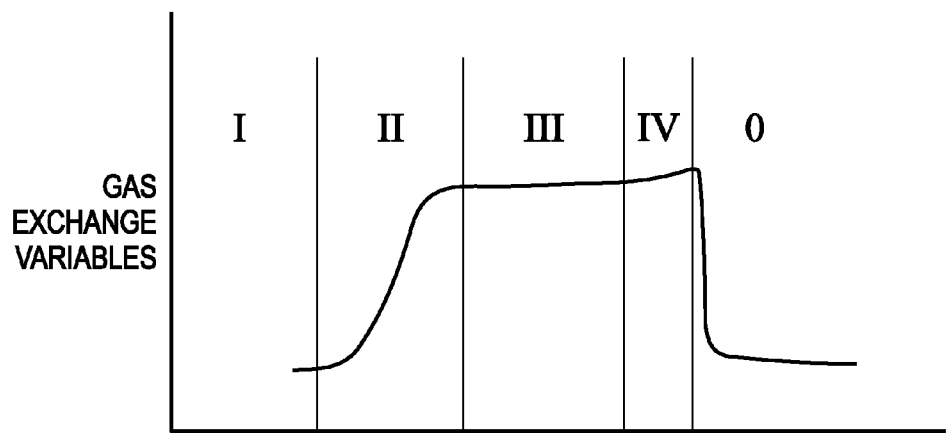
FIGS. 6A and 6B illustrate gas exchange patterns during a respiratory cycle, illustrating an example gas exchange pattern indicating a trachea.
Figure 6B:
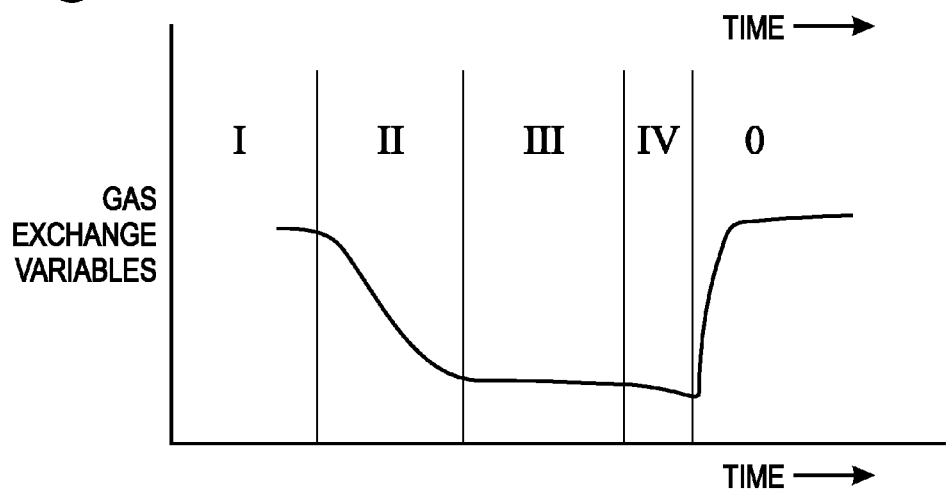

In some embodiments, the trachea identifying device may be an airway sensor and the pattern may be a gas exchange pattern. The gas at the trachea opening, the vocal cords, or the trachea demonstrate the gas exchange pattern while the gas exchange pattern is absent in the esophagus opening. FIGS. 6A and 6B illustrate gas exchange patterns during a respiratory cycle, illustrating an example gas exchange pattern indicating a trachea opening or a trachea. Human breathing consists of inhalation and exhalation or a breathing cycle or a respiratory cycle. A respiratory cycle is dynamic and typically occurs twelve (12) to twenty (20) times per minute. Inhalation and exhalation result in gas exchange or air exchange between a respiratory system of a human and ambient air. The gas exchange occurs in the trachea while there is no gas exchange in the esophagus. As such, a gas exchange pattern can be used to identify the trachea.

A respiratory cycle can be divided into five phases. The phase 0 is an inhalation phase with an inflow of ambient air. In the phase I, exhalation begins as air in the respiratory system flows out, with dead space ventilation. In the phase II, exhalation continues with the mixing of dead space and alveolar gas. In the phase III, air continues to flow out but alveolar gas is stabilized. In the phase IV, the outward airflow decreases and the exhalation ends. As illustrated in FIGS. 6A and 6B, each phase can be characterized by the changes of the gas exchange variables associated with the inhaled and exhaled air, such as air flowrate, air pressure, $CO_2$ and $O_2$, $N_2$, or humidity, etc.

Some gas change variables are at a lower level in the ambient air but the level increases after exchanging with gas in the lungs. Such variables include $CO_2$, temperature and humidity. FIG. 6A illustrates an example gas change pattern of $CO_2$, temperature and humidity. The Phase 0 is an inhalation phase with an inflow of ambient air. When air is flowed into the airway, $CO_2$ concentration is at the atmosphere level, i.e., approximately 0.04% $CO_2$ in the airflow. Similarly, the temperature and humidity are at the ambient temperature (e.g., room temperature of 24° C.) or ambient humidity. In the phase I, the air starts flowing out but the $CO_2$, temperature and humidity are still at the atmosphere level. In the phase II, as the air starts flowing out from the trachea, the gas exchange variables, such as $CO_2$ concentration, temperature and, humidity vary. For example, the expired air has higher temperature than the inspired air due to heat exchange in the lungs. Further, the expired air has higher vapor than the inspired air due to fluid exchange in the lungs. Similarly, $CO_2$ concentration increases after gas exchange in the lungs. FIG. 6A shows that gas exchange variables (e.g., $CO_2$ concentration, temperature, and humidity) increase rapidly. In the phase III, the $CO_2$ concentration, temperature and humidity continue to increase slowly. The $CO_2$ concentration may be reached a level of 5% $CO_2$, the temperature may rise to 32° C. and the humidity may be up to 5% of water content. In the phase IV, the $CO_2$ concentration, temperature and humidity continue to increase to the highest level of the respiratory cycle.

It should be noted that the air flow or pressure may follow the similar pattern illustrated in FIG. 6A. For example, the exhaled air flowrate and air pressure increase and then decrease during the exhalation phase.

The gas change variables, such as oxygen are at a higher level in the ambient air but the level decreases after exchanging with gas in the trachea. FIG. 6B illustrates an example gas change pattern of $O_2$ during the respiratory cycle. In the phase 0, air flows into the airway and the $O_2$ concentration is at the atmosphere level, i.e., approximately 21% $O_2$ in the airflow. In the phase I, the air starts flowing out but $O_2$ concentration is still at the atmosphere level. In the phase II, $O_2$ concentration decreases quickly and may be lowered to 14% $O_2$. In the phase III, $O_2$ concentration continues to decrease. In the phase IV, $O_2$ concentration decreases to a lowest level of the respiratory cycle.

It should be noted that the gas change pattern is not limited to the examples described above. Any detectable pattern during a respiratory cycle may be used to identify the trachea. Further, the characteristics of inhaled air may be modified to make the pattern more discernable. For example, the temperature, humidity, oxygen concentration of the inhaled air may be adjusted to a predetermined value and delivered through intubation system or a face mask to the patient such that desired variations of the temperature, humidity, oxygen concentration during the respiratory cycle can be obtained. In one example, the temperature of the inhaled air may be lowered and the $O_2$ concentration of the inhaled air may be increased to create greater temperature and the $O_2$ concentration differential if desired.

As described above, the gas exchange data, such as $CO_2$ and $O_2$ concentrations, temperature, airflow, or pressure can be detected by an appropriate gas exchange detector. The detected gas exchange data may be presented in a graphical format as shown in FIGS. 6A and 6B to display the gas exchange pattern. The presence of the gas change pattern can indicate that the guide stylet is adjacent to the trachea opening or in the trachea. Thus, the gas exchange pattern as shown in FIGS. 6A and 6B can be used as navigation guidance.

Additionally, the detected data can be analyzed for the gas exchange pattern indicating the trachea. The gas exchange features may include, but are not limited to, $CO_2$ or oxygen concentration at a predetermined threshold, temperature, humidity, flowrate or pressure at a predetermined level. The gas exchange features may further include abrupt changes of the gas change data from the phase I to the phase II or from the phase IV to the phase 0. The gas exchange features may further include a continued increase or a continued decrease of detected gas exchange data during the phase II, III or IV.

As described above with reference to the topographical pattern, any appropriate data analysis techniques may be used to identify the gas exchange pattern indicating the trachea. For example, the pattern matching may be used by comparing the detected gas exchange data with a predetermined gas exchange pattern, threshold values, other gas exchange features. In another example, the gas exchange pattern indicating the trachea may be determined by pattern recognition based on the gas exchange features. The pattern recognition may be based on supervised learning or unsupervised learning as described above. The navigation guidance may be generated based on the gas exchange data analysis.

Alternatively, or additionally, a sound pattern may be used to identify the trachea. In one example, the intubation system is patient specific and can learn a patient's voice by recording the patient's sound before the intubation and the sound can be stored and recognized by the intubation system using any voice recognition technology. During the intubation, the patient can be asked to generate sounds, such as "aaa, eee, woo." A sound detector, such as a microphone or an acoustic camera can be used to detect the sound. The intubation system can match the detected sound with the stored sound pattern and generate the navigation guidance.

Figure 7:
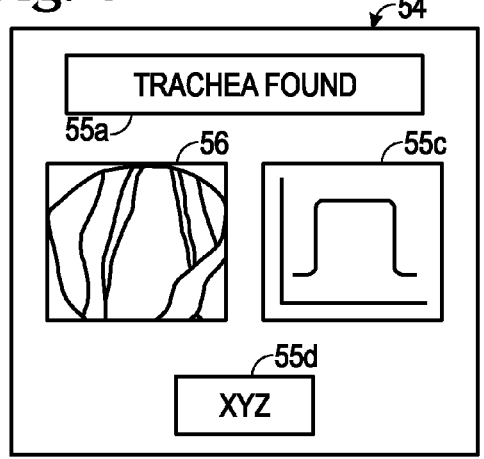
FIG. 7 shows an example navigation guidance of an intubation according to the present disclosure.

FIG. 7 shows examples of navigation element displayed as shown on a display device 54 of an intubation system according to one embodiment of the present disclosure. The navigation element 55 may include one or more user viewable navigation guidance displays to direct the movement of a guide stylet of the intubation system. As described above, navigation element 55 is generated based on the analysis and or processing of the detected data related to the trachea. During the intubation, navigation element 55 may be presented dynamically in display device 54 as the guide stylet moves in a patient's airway. In one example, navigation element 55 may be displayed as a statement 55a, such as "Trachea found" when the trachea is identified based on the detected data. Likewise, navigation element may be displayed as "Trachea not found" when the guide stylet is not in a position of a trachea opening or in the trachea.

In another example, navigation element 55b may be shown as an image of the trachea opening, an esophagus, and their surrounding. Navigation element 55b may be a thermal image, a video image, or a processed image. A user can identify the trachea via the topographical features described above or can identify the trachea by observing the variations in a respiratory cycle, such as the color variation of the glottis in a thermal image during a respiratory cycle and the motion of the vocal cords during phonation. In yet another example, navigation element 55c may be a gas exchange pattern. The user can determine whether the guide stylet is in the trachea by observing the gas exchange pattern. In still another example, navigation element 55d may include instructions, such as directions on how to move the guide stylet. In another example, navigation element 55d may be a directional movements enabled by a control of the intubation system. In another example, the navigation element may include a captured image with a target, such as a block (not shown) that continues to move and target the trachea in the image. It should be appreciated that one or more examples of navigation element illustrated can be presented in display device 54 simultaneously depending on the trachea identifying device and data analysis of the intubation system.

FIG. 8 shows an example embodiment of blade 42 and guide stylet 46 according to the present disclosure. Blade 42 may have various shapes and dimensions. In the depicted embodiment, blade 42 is curved and is sized to have a length L such that a distal end 43 of blade 42 is adjacent to a trachea opening when blade 42 is placed into a patient's mouth. Further, a width of the blade may be configured to receive the guide stylet and the ETT and adapted to accommodate the guide stylet's movement along the blade and an insertion of the endotracheal tube over the guide stylet. A shape of blade may be adapted to facilitate moving a patient's tongue forward and upward. In this way, blade 42 may be used as a guide rail to facilitate the guide stylet's movement. Guide stylet 46 can be extended from distal end 43. In the extended position, distal end 43 may be used as a fulcrum for a tip portion of guide stylet to perform the desired movements.

In some embodiments, blade 42 may include a bottom wall 80 as the guide rail for the forward and backward movement. Additionally, blade 42 may include a side wall 82 extending from the bottom wall such that guide stylet 46 is moved against side wall 82 without deviating from an insertion direction or moving away from the blade. In other embodiments, blade 42 may include a top wall 86 to define the guide stylet's up and down movement and to avoid a bite of the guide stylet by the patient. Alternatively, blade 42 may include another side wall (not shown) opposite to side wall 82 such that guide stylet 46 is enclosed along its length. Openings 84 may be incorporated into side wall 82 to allow the observation of the guide stylet's movement and the ETT movement. It should be appreciated that blade 42 may be in straight configuration or blade 42 may have any desired length.

Guide stylet 46 may be configured to be moved in multiple degrees of freedom (DOFs). For example, guide stylet 46 may perform "up and down movement" referred to as a first DOF, "right and left movement" referred to as a second DOF, and "forward and back movement" referred to as a third DOF. The multiple DOF movements may be caused by a drive mechanism via activation of an actuator on the intubation system by a user. Alternatively, the multiple DOF movements may be caused by a drive mechanism automatically via a controller of the intubation system. Alternatively, a user may move the guide stylet manually to perform the multiple DOF movements.

Figure 9:
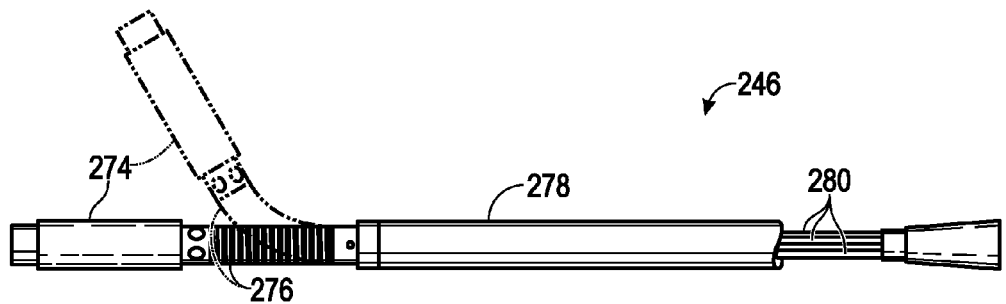
FIG. 9. shows another example embodiment of guide stylet of the intubation system according to the present disclosure.

FIG. 9 shows another example embodiment of a guide stylet 246 according to the present disclosure. Guide stylet 246 typically includes a tip portion 274, a joint portion 276 and a guide stylet body 278. The trachea identifying devices, such as an image capture device, a gas exchange detector and a light source may be disposed on or attached to tip portion 274 as described above with reference to FIG. 4. The trachea identifying devices can generate information related the surroundings of tip portion 274. For example, the attached image capture device has a line of sight as seen from tip portion 274 and sees a view in front of tip portion 274. In another example, the gas exchange detector senses the conditions surrounding or adjacent to tip portion 274. When tip portion 274 is in a trachea opening or in the trachea, the attached gas exchange detector can sense the gas exchange characteristics or gas exchange patterns.

Joint portion 276 has a predetermined length and is capable of being deflected in any directions. Joint portion 276 may be made of flexible materials or made of rigid material, such as metal in a coiled form.

Stylet body 278 is shown to include a tube and a plurality of cables 280 disposed inside the tube. Cables 280 may include a light bundle (e.g., fiber optics) and/or a camera cable. In some embodiments, cables 280 may include direction control cables that can be articulated by a drive mechanism to direct tip portion 274 to a desired direction. The articulation of the direction control cables may adjust the direction of the tip portion, and thus enable multiple DOFs movement of the guide stylet.

It should be appreciated that the guide stylet may have various configurations. For example, the tip portion, the joint portion and the guide stylet body may be made from different materials with different rigidities. Alternatively, the tip portion, the joint portion and the guide stylet body may be made from the same material and may be rigid or flexible along the length of the guide stylet. Further, it should be appreciated that the guide stylet may be used together with a blade in the intubation system according to the present disclosure. As described in the present application, the blade may facilitate the multiple DOF movements of the guide stylet. Alternative, the guide stylet may be used alone without the blade for the trachea identification.

FIGS. 10A and 10B show a cross section view of an intubation system 100 according to another embodiment of the present disclosure, illustrating a blade, an ETT compartment and a drive mechanism. As shown in FIGS. 10A and 10B, intubation system 100 may include a blade 142 and a guide stylet 146 disposed inside blade 142. Blade 142 may include a body 102 having a distal end 108. Blade 142 is formed of a curved shape toward the distal end or as shown or along its length. Blade 142 may include a bottom wall 104 and a side wall 106. Bottom wall 104 may be configured to have a length L such that distal end 108 of bottom wall 104 is located adjacent to a trachea opening or an esophagus opening during an intubation. In some embodiments, blade 142 may further include a top wall 110 and a side wall (not shown). Blade 142 may be configured to have three walls and leave one side open to facilitate an ETT balloon wire (not shown) and visual observation of the insertion of ETT 52 and/or guide stylet 146. Bottom wall 104, top wall 110 may be configured to have a shape to accommodate the insertion of the guide stylet and the ETT and have less trauma to the patient.

Blade 142 may be rigid and made of metal or plastic materials of sufficient strength. Because of the rigidity, bottom wall 104 can function as a guide rail to facilitate the third DOF movement (i.e, forward and backward) of guide stylet 46. In some embodiments, distal end 108 may serve as a fulcrum or a pivot point for a first DOF movement of guide stylet 46 (e.g., up and down). Similarly, a distal end of side wall 106 and side wall 112 may serve as a fulcrum for the second DOF movement of guide stylet 46 (e.g., right and left).

In some embodiments, blade 142 may be releasably connected to the intubation system via any appropriate connections, such as a screw, a snap fitting, a clip fitting or a solenoid. A user of the intubation system can select the blade adapted for a specific patient group, such as adults or children. The blade may be reusable.

ETT 52 may be preloaded or loaded from the distal end 108 of blade 142 into an ETT compartment 148. In the depicted embodiment, a rear portion of guide stylet 146 is disposed inside the ETT at ETT compartment 148. A front portion of guide stylet 146 is substantially positioned at a center portion of blade 142. In some embodiments, guide stylet 146 is suspended along a portion blade 142. The suspension means that there is a space or a gap 111 between the guide stylet and blade such that the ETT can be inserted into the blade and slipped over the guide stylet or there is no physical connection between the guide stylet and the blade. Although the guide style is suspended, the guide stylet can make physical contact with the blade for moving along the blade by a user or by a drive mechanism or move along a length of the blade. The positioning of the guide stylet allows an ETT to be slipped over the guide stylet and move along the guide stylet. As ETT 52 is positioned substantially concentric with guide stylet 146 at an insertion direction or a longitudinal axis of ETT 52 and guide stylet 146, the moving path of ETT 52 is aligned with guide stylet 146. In this way, ETT 52 can be moved into the trachea following guide stylet 146. In other words, the intubation system can intubate as long as the trachea is "seen" or identified.

In some embodiments, blade 142 may be disposable so that blade 142 may remain in the patient's mouth as a bite blocker to prevent the patient's biting on the ETT during the medical procedure. Blade 142 may be made of disposable materials, such as plastic. Blade 142 and ETT 52 may be configured to be a disposable package for one intubation. For example, blade 142 and ETT 52 may include a locking mechanism, such as a clip fitting to couple blade 142 with ETT 52 together once the ETT 52 is inserted into the trachea. In this configuration, blade 42 may be first connected to insertion guide device 144 or an ETT compartment 148. Then, ETT 52 may be preloaded into ETT compartment 148 from the distal end 108 of blade 142.

In some embodiments, an ETT may have multiple segments and each of the segments is adapted for a single use for one intubation. The ETT with the multiple segments may be preloaded separately or in one integral tube with a predetermined length of segments separable via any appropriate mechanism (e.g., via cutting) in a folded form in ETT compartment 148. During an intubation, one ETT segment is separated from the rest of the ETT segments and the remaining ETT segments can be kept in ETT compartment for the next use.

FIG. 10A also illustrates a target point P and a light path M generated by a precision light guide 70, such as a laser pointer located on guide stylet 146. The light from the laser pointer is directed to the trachea opening as represented by point P when the trachea is located. ETT 52 can be inserted toward the trachea opening following the target point P and the light path M. As such, ETT 52 can be inserted correctly into the trachea even if blade 142 has a curved configuration, ETT has to be inserted from a poor angle, or ETT 52 has to be pushed from a place far behind blade 42.

FIG. 10A shows an unlocked position of guide stylet 146 and ETT 52 and FIG. 10B shows a locked position of guide stylet 146 and ETT 52. In the depicted embodiment, guide stylet 146 is locked by a guide stylet locking solenoid 114 after ETT 52 is preloaded into ETT compartment 148. As guide stylet locking solenoid 114 is energized, guide stylet 146 is coupled with a drive mechanism 116 to enable the motorized movement of the guide stylet. Drive mechanism 116 includes a leadscrew 118 that is driven by a motor 120 via a drive gear 122. In the depicted embodiment, leadscrew 118 may cause the third DOF movement of guide stylet 46, that is, forward and backward movement of guide stylet 146. The third DOF causes the guide stylet to withdraw from a current position for preparing movement in a different direction and then causes the guide stylet to move forward. The drive mechanism including the leadscrew can move the guide stylet in a predetermined distance with desired precision.

Any appropriate drive mechanism can be used to perform the third DOF movement. Referring to FIG. 11, an example roller motor driven mechanism 400 is illustrated. For example, roller motor driven mechanism 400 may be used to cause the third DOF movement. Roller motor driven mechanism 400 may include a drive gear 420 motorized by a motor 410. Drive gear 420 engages with a driven gear 430 to cause a guide stylet 146 to move forward and backward relative to an engagement point. In the depicted embodiment, roller motor driven mechanism 400 may further be adjusted to receive an ETT 52 and cause ETT 52 to move forward and backward. Roller motor driven mechanism 400 may allow the guide stylet or ETT to move in a longer distance compared to the drive mechanism including the leadscrew. As another example, a telescoping mechanism may be used to perform the third DOF movement.

Returning to FIGS. 10A and 10B, drive mechanism 116 may further include a second motor 123 to perform the first DOF movement. Second motor 123 may cause the first DOF movement by deflecting or articulating the guide stylet in a predetermined direction, i.e., up and down relative to the insertion direction. In one embodiment as described above with reference to FIG. 6, the guide stylet includes a directional cable. The articulation of the guide stylet may be accomplished by deflecting the directional cable. Similarly, drive mechanism 116 may include a third motor 125 to perform the second DOF movement and third motor 125 may cause the second DOF movement by deflecting the guide stylet in a predetermined direction, i.e., right and left relative to the insertion direction. Alternatively, four motors may be used to articulate the tip portion of guide stylet to perform multiple DOFs movements using a technique known in the art.

It should be appreciated that the third DOF movement may be translated forward and backward movement of the guide stylet or may be rotated forward and backward movement of the guide stylet. Likewise, the first DOF movement may be translated up and down movement of the guide stylet or may be rotated up and down movement of the guide stylet, and the second DOF movement may be translated right and left movement of the guide stylet or may be rotated right and left movement of the guide stylet or snake-like movement.

The multiple DOFs movements manipulate the guide stylet to move in the desired directions. For example, the third DOF movement can cause withdrawal of the guide stylet in a predetermined distance once it is determined that the trachea is not identified. The controlled withdrawal followed by the forwarding movement in an adjusted direction allows quick maneuver of the guide stylet. Further, the guide stylet can restart the search for the trachea from a predetermined point following the withdrawal. In this way, it is not necessary to withdraw the guide stylet substantially away from a place adjacent to the trachea or esophagus and initiate an insertion attempt again. Further, the semi-automatic or automatic intubation makes it possible to intubate a patient with one hand.

In some embodiments, ETT 52 may be moved by an ETT drive. As shown in FIG. 10A, ETT 52 is preloaded in an ETT shuttle 124. FIG. 10A shows that ETT 52 is unlocked as ETT locking solenoid 126 is de-energized. FIG. 10B shows that ETT 52 is locked as ETT locking solenoid 126 is energized. In the locked position in FIG. 10B, ETT may be moved forward and backward in ETT shuttle 124 as shown by arrows. In the depicted embodiment, ETT 52 can be pushed into the trachea automatically by the ETT shuttle. Alternatively, ETT 52 may be inserted into the trachea manually.

Figure 12A:
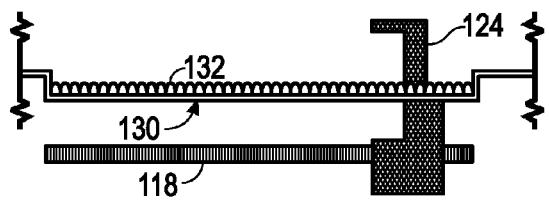
FIGS. 12A, 12B, and 12C illustrate example embodiments of a seal used in an endotracheal tube compartment of an intubation system according to another embodiment of the present disclosure.

ETT compartment 148 may be separated from a main compartment 128 of insertion guide device 144 by a seal 130 to form an isolated compartment. FIG. 12A illustrates one embodiment of seal 130 that includes an accordion structure 132. Accordion structure 132 allows the seal extend or extract along its length such that ETT compartment 148 remains sealed during the movement of ETT shuttle 124.

Figure 12B:
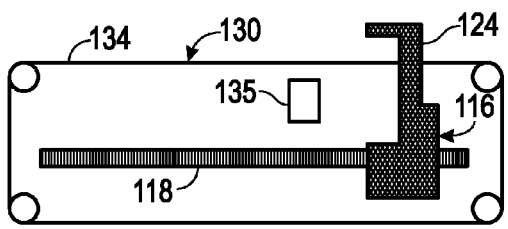

FIG. 12B illustrates another embodiment of seal 130. A large elastomeric band 134 is shown to enclose the components, such as a drive mechanism 116 and electronic components 135.

Figure 12C:
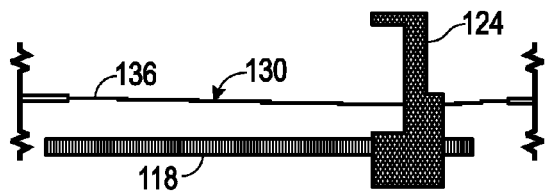

FIG. 12C illustrates yet another embodiment of seal 130. Seal 130 is shown to include a plurality of sheets 136 which are connected to each other and movable relative to each other along a direction of the shuttle movement. In this way, ETT compartment 148 is separated from the main compartment 128 despite the shuttle movement.

ETT compartment 148 may further include a detachable mechanism, such as a clip or a snap fitting to remove ETT compartment 148 from the intubation system. The detachable mechanism may separate ETT compartment 148 from the drive mechanism and other components of the intubation system.

ETT compartment 148 may need to be sterilized to receive ETT 52 before an intubation procedure. A sealed compartment prevents fluid used for sterilization to enter into the main compartment 128. As such, components in contact with ETT 52, such as guide stylet and ETT compartment 148 can be sterilized without affecting the electronic and mechanical components of the intubation system. That is, ETT compartment 148 is water sealed for sterilization. Further, the guide stylet and the ETT compartment may be removed from the intubation system for sterilization independently and then be reinstalled into the intubation system.

In some embodiments, an ETT compartment may not be included in the intubation system. The guide stylet may be loaded with an ETT or with a plurality of ETT segments, each segment for one intubation. A portion of the guide stylet in contact with other components of the insertion guide device is water sealed from the electronic components and drive components for sterilization.

Figure 13:
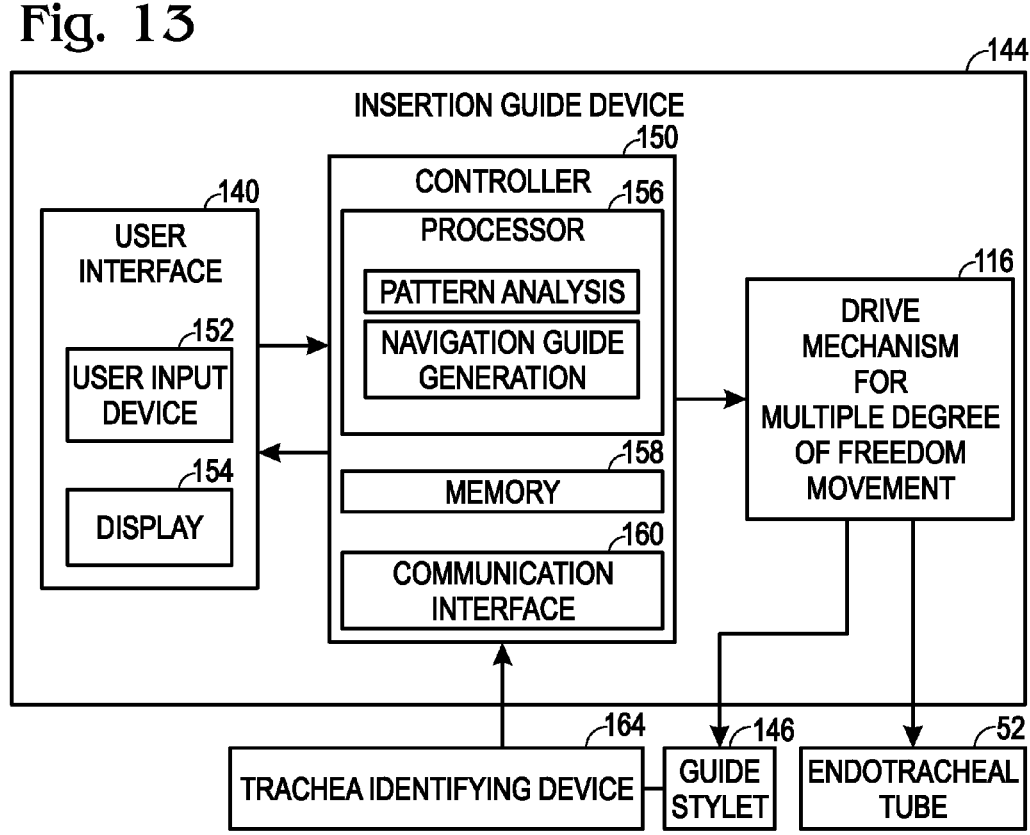
FIG. 13 is a schematic diagram of an intubation system according to the present disclosure.

FIG. 13 is a schematic diagram of an intubation system 100 according to one embodiment of the present disclosure, illustrating example components of the intubation system. As illustrated in FIG. 13, insertion guide device 144 may include a user interface 140 and a controller 150. User interface 140 may include a user input device 152 to activate and operate intubation system 40. Further, user interface 140 may include a display device 154 to present information, such as the navigation element for the operation of the intubation system.

Controller 150 may be a microcomputer including a microprocessor unit or data processor 156, an electronic storage medium or a memory 158, and a communication interface 160. Data processor 156 and communication interface 160 may be linked by a bus to memory 158. Controller 150 may also be configured to communicate with a trachea identifying device 164 via communication interface 160. Trachea identifying device 164 may be one of a gas exchange detector, an image capture device, a sound detector, and a light detector. In some embodiments, memory 158 may include both non-volatile and volatile memory, and programs or algorithms may be stored in non-volatile memory and executed by the processor using portions of volatile memory to accomplish data analysis and the operations described herein. Storage medium read-only memory may be programmed with computer readable data representing instructions executable by the microprocessor for performing the data analysis and methods described in the present disclosure as well as other variants that are anticipated but not specifically listed. For example, the controller may receive communication (e.g., input data) from the various sensors, process the input data, and trigger the actuators in response to the processed input data based on instruction or code programmed therein corresponding to one or more routines.

In some embodiments, the intubation may be performed manually. As described above, trachea identifying device 164 may be disposed on guide stylet 146. When intubation system 100 is activated, a user may insert guide stylet 146 into the patient's mouth or nostril and then adjust a position of guide stylet 146 based on the displayed navigation guidance. Additionally, or alternatively, the user may insert guide stylet 146 at his/her discretion.

In some embodiments, guide stylet 146 may be configured to move semi-automatically or automatically. Intubation system 100 may further comprise a drive mechanism 116 operatively coupled to guide stylet 146 and controller 150. Controller 150 may be configured to communicate with trachea identifying device 164 and drive mechanism 116 via communication interface 160 to perform various operations described herein.

Drive mechanism 116 may be configured to cause desired movements of guide stylet 146 and/or manually, semi-automatically, and/or automatically, and may include one or more motors, drives, etc. In one example, desired movements may include, but are not limited to, the first DOF movement (e.g., forward and backward), the second DOF movement (e.g., up and down), the third DOF (e.g., right and left), or the movements in any direction or any angle relative to a guide stylet position. The guide's motion may include, but is not limited to linear motion, 360° rotation, or combinations thereof. In some embodiments, a tip portion of guide stylet 146 may be configured to perform steering motions, such as moving in any direction and guide stylet is configured to follow the tip portion In some embodiments, the guide stylet's movements may be fully automated. For example, controller 150 may be configured to include a program or an algorithm to move guide stylet 146 based on information from trachea identifying device 164. As described above, the information may include a level of temperature, $CO_2$, $O_2$, sound, light, a gas exchange pattern, or a topographical pattern. In some embodiments, when guide stylet 146 is inserted into a patient's mouth or nose and intubation system 144 is activated, the tip portion of guide stylet 146 may be automatically moved forward and its position may be automatically adjusted in any desired directions relative to the position of guide stylet 146 to search for the trachea. It should be appreciated that guide stylet 146 may be configured to perform any suitable movements to search for the trachea and move into the trachea. Further, it should be noted that any suitable known method known in the art may be used to enable the automated movements.

In some embodiments, the guide stylet's movements may be performed semi-automatically. For example, the movements may be actuated through user input device 152. User-directed movements such as forward, backward, up, down, right or left movements in any direction relative to the tip portion of guide stylet 146 may be actuated by a user using corresponding actuators on user input device 152.

Additionally, the use-directed movements and/or automated movements may be guided by information, such as the navigation element presented on display device 154. Alternatively, the movement may be activated or controlled by a user using a computing device via a network connection.

The easy trachea identification and the motorized movement of the guide stylet of the intubation system simplify the intubation and increase the success rate of the intubation.

Additionally, or alternatively, intubation system 100 may be configured to permit the user interaction during the automated or semi-automated intubation process. For example, the automated guide movement may be overridden by a user's input at any time. In this way, the intubation may be further refined by the user.

Figure 14:
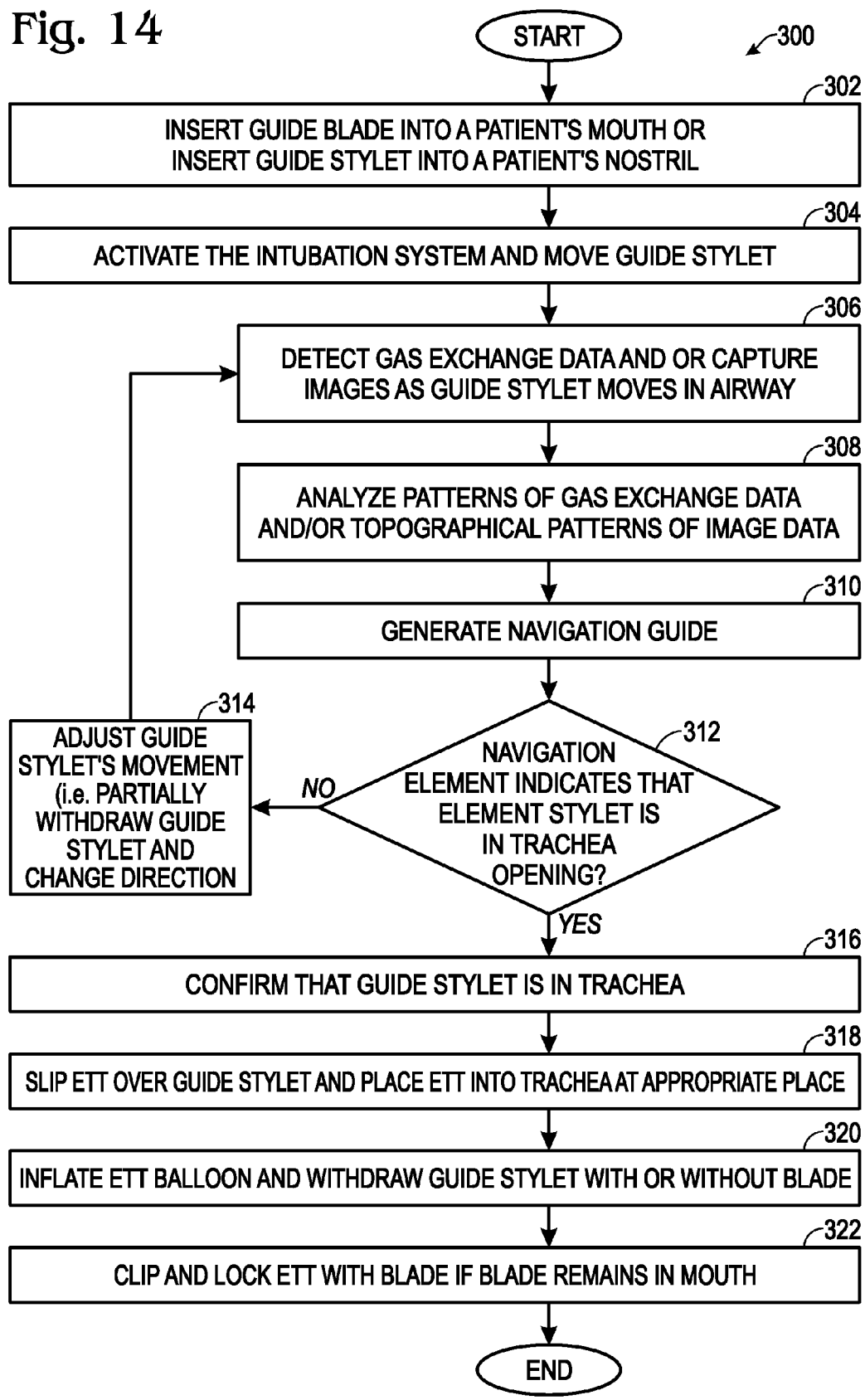
FIG. 14 is a flowchart illustrating an example method to intubate a patient using an intubation system according to one embodiment of the present disclosure

FIG. 14 is a flowchart illustrating an example method 300 to intubate a patient using an intubation system according to one embodiment of the present disclosure. At 302, the method includes inserting a guide stylet into an upper airway of a patient. If the intubation is performed via a patient's nose, the guide stylet is inserted into a patient's nostril. If the intubation is performed via a patient's mouth, the blade may be inserted into the mouth and the blade may stop at a location adjacent a trachea opening or an esophagus opening when the blade is inserted into the patient's mouth. In some embodiments, before 302, the method includes preloading an ETT into the guide stylet or preloading the ETT into an ETT compartment of the intubation system for a pre-intubation step.

Next, at 304, the method includes activating the intubation system and moving the guide stylet. As described above, a moveable guide stylet may be positioned inside the blade with a trachea identifying device disposed on a tip portion of the guide stylet. In some embodiments, the guide stylet may be positioned at a center portion of the blade and suspended along the length of the blade. Alternatively, the guide stylet may be moved by a drive mechanism at the user's control via an actuator or by a controller automatically.

In some embodiments, the trachea identifying device may detect airway data. For examples, the airway data may include image data or gas exchange data and the trachea identifying device may be an image capture device to detect image data or a gas exchange detector to detect gas exchange data. At 306, the method includes detecting gas exchange data by the gas exchange detector and/or capturing image data by the image capture device as the guide stylet moves in the airway.

At 308, the method analyzes or displays a gas exchange pattern of the detected gas exchange data and/or a topographical pattern of the detected image data. Any appropriate data analysis techniques can be used to determine the presence of a pattern indicating the trachea opening. As described above, the pattern matching or pattern recognition may be used. Alternatively, the detected gas exchange data may be presented in a graphical pattern that can easily identify the trachea, such as the patterns illustrated in FIGS. 6A and 6B. In another example, the captured image, such as a thermal image may be displayed directly as shown in FIGS. 5A and 5B.

Next, at 310, the method generates a navigation element based on the detected data or data analysis. The navigation element may include an indication, such as "trachea found" or "trachea not found." Alternatively, the navigation guidance may be a pattern indicating the trachea opening or the trachea.

At 312, it is determined whether the navigation element indicates that the guide stylet is the trachea opening. If the answer is no, the method goes to 314 to adjust the guide stylet's movement. In one example, the adjustment may include withdrawing the guide stylet partially and then changing the moving direction. In another example, the guide stylet may be adjusted from the third DOF movement (e.g., forward and backward) to the first DOF movement (e.g., up and down) to the second DOF movement (e.g., right and left). From 314, the method goes to 306 to repeat the steps of the data detection and analysis.

If the answer at 312 is yes, the method continues to 316 to confirm that the guide stylet is in the trachea. In some embodiments, the trachea location may be confirmed by repeated indication from the navigation element based on the same type of detected airway data. In other embodiments, the navigation element generated from different type of the detected airway data may be used confirm the determination. For example, the navigation element based on a topographical pattern may indicate that the guide stylet is in front of the trachea opening. After the determination that the guide style is in the trachea opening, a second navigation element based on a gas exchange pattern, such as a $CO_2$ pattern may be used to confirm that the guide stylet is in the trachea.

Next, at 318, the ETT is slipped over the guide stylet and is placed in the trachea at an appropriate position. Steps 304 and 318 constitute an intubation stage.

Next, at 320, the method includes inflating an ETT balloon and withdrawing the guide stylet with or without the blade. In some embodiments, the blade is disposable and remains in the mouth as a bite blocker. If the blade remains in the mouth, the method includes clipping and locking the ETT with blade. The steps 318 and 320 constitute a post-intubation stage.

The method described above enables an automatic or semi-automatic movement of the guide in response to the navigation guidance generated from real time data. Thus, the position of the guide stylet can be continually adjusted through feedback from the navigation guidance. In this way, the guide stylet can be accurately and quickly inserted into the trachea.

It should be appreciated that the method can be used in an intubation system including a $CO_2$ sensor, an $O_2$ sensor, an airflow sensor, a pressure sensor, a temperature sensor, a light sensor or a sound detector. The navigation element can be generated based on information from one of a $CO_2$ sensor, an $O_2$ sensor, a temperature sensor, a light sensor or a sound detector.

Figure 15:
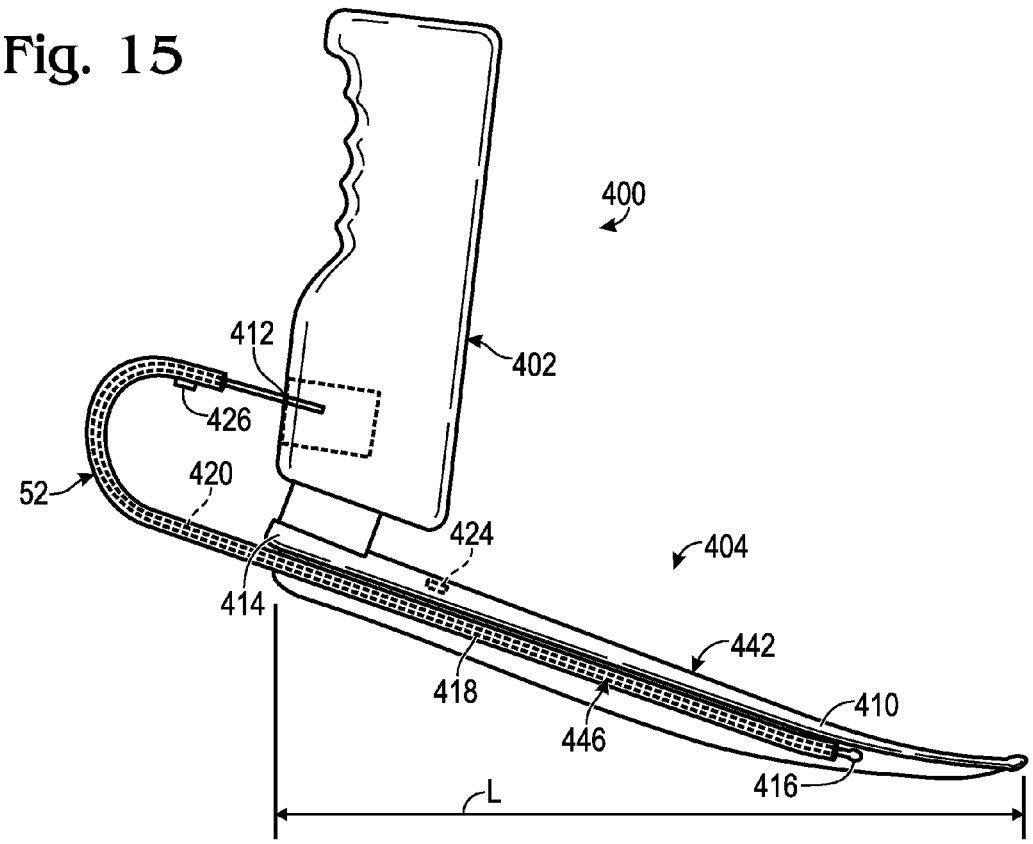
FIG. 15 is an elevation view of an example intubation device according to another embodiment of the present disclosure.

FIG. 15 shows an example intubation device 400 according to another embodiment of the present disclosure. Intubation device 400 may be configured to enable an ETT 52 to be arranged in-line with a guide stylet 446, referred to as an in-line alignment or an in-line arrangement herein. That is, ETT 52 can move in a path the same as a moving path of guide stylet 446. Intubation device 400 includes an insertion guide device 402 and a blade body 404. Insertion guide device 404 may include electronic components for identification of a trachea opening or a trachea.

Blade body 404 may include a blade 442. Blade 442 may be any shape suitable to insert into an upper airway of a patient and facilitate moving a patient's tongue forward and upward. Further, Blade 442 may be sized to receive ETT 52. In the depicted embodiment, blade 442 has a concave surface to form a hollow space under the surface and the blade is curved toward a distal end 410. In one example, blade 442 may have a length L such that distal end 410 is positioned adjacent to a patient's trachea opening when blade 442 is inserted into a patient's mouth. A width of the blade may be sized to facilitate a movement of ETT 52 along the blade. Alternatively, blade 442 may be any appropriate shape for intubation, such as a conventional laryngoscope blade. In one embodiment, blade body 404 is releasably connected to insertion guide device 402.

Intubation device 400 may include guide stylet 446. In some embodiments, guide stylet 446 may fixed at a mounting portion 412 at insertion guide device 402. Alternatively, guide stylet 446 may fixed at blade body 402. Guide stylet 446 is suspended along a length of blade 442 adjacent or under the concave surface of the blade. In some embodiments, guide stylet 446 may be positioned substantially centrally along the length of blade 442 and may be suspended along an entire length of the blade and extended over a proximal end 414 of the blade. In some embodiments, guide stylet 446 may include a tip 416 adjacent to distal end 410 of the blade, a first section 418 disposed along the length L of the blade and a second section 420 extending between mounting portion 412 and proximal end 414 of the blade. Guide stylet 446 may be made of rigid materials, such as metal or hard plastic to have stiffness required to be suspended substantially stationary. In some embodiments, the guide stylet can be suspended rigidly with the support at one point or is suspended substantially at a fixed position via the support at one location. Guide stylet 446 is coupled with other components of intubation device mechanically, electronically or optically.

In the depicted embodiment, the guide stylet is substantially stationary or has zero degree of freedom movement. In some embodiments, first section 420 of the guide stylet is configured to have a sufficient length between mounting portion 412 and proximal end 414 of the blade such that a total length of the guide style is greater than a length of the ETT 52 to allow preloading or loading of ETT 52 along the guide stylet. ETT 52 may be preloaded to ETT loading section 420 from distal end 410 of the blade. In some embodiments, guide stylet 442 may be releasably connected to the insertion guide device and may be detachable for sterilization or replacement.

As shown in FIG. 15, ETT 52 can be moved over guide stylet 446 toward distal end 410 of the blade. As such, ETT 52 can be pushed into the airway along the guide stylet.

In some embodiments, blade 442 may be disposable and made of materials, such as plastic. Further, blade 442 may be remained in the patient's mouth as a bite blocker. Blade 442 and ETT 52 may be locked together by a locking mechanism once the intubation is completed. For example, as shown in FIG. 9, blade 442 may include a clip 424 and ETT 52 may include a complementary clip 426 to couple blade 442 and ETT 52 together. Any appropriate locking mechanism may be used to lock the blade with the ETT.

In some embodiments, a trachea identifying device, such as a light source or a video camera may be disposed on a tip 416 of guide stylet 446. The trachea identifying device is coupled to the insertion guide device electronically and/or optically. A trachea opening may be identified through a direct view of the trachea opening via illumination provided by the light source or identified through an indirect view of the trachea opening via an image captured by the video camera. In other words, the trachea opening may be identified by a view of an airway pattern or a topographical pattern. As the ETT is aligned in-line with the guide stylet, the ETT is in a line of view the same as that of the guide stylet. In other words, it can be intubated as long as the trachea opening can be identified.

The precision of an ETT insertion into the trachea opening may further be improved by using a precision light guide (not shown). In some embodiments, tip 416 of the guide stylet may include a precision light guide, such as a laser pointer or other light pointers located on guide stylet 146. The light ray from the laser pointer is directed to the trachea opening once the trachea opening is identified by the trachea identifying device in tip 416 of the guide stylet. ETT 52 can be pushed toward the trachea opening following the light ray. As such, ETT 52 can be inserted correctly into the trachea.

It should be appreciated that any appropriate trachea identifying device can be used. For example, the trachea identifying device may be an airway sensor, such as a light source, an image capture device, a gas exchange detector, a sound detector or a light detector as described above. In one example, the airway sensor may generate an airway pattern viewable to a user and the trachea opening may be identified by airway features indicated or displayed on the airway pattern. For example, in some embodiments, the airway sensor may be an image capture device, such as a video camera or a thermal camera to capture and display the images of the airway pattern including the image of the trachea opening, the esophagus opening and their surroundings. The trachea opening may be identified based on airway features or topographical features of the trachea opening. The topographical features may include an inverted V shape of vocal cords, white color of the vocal cords, vocal cord folds vibration, and vocal cord's spatial relationship to its surrounding structures, such as epiglottis, a glottis, and arytenoids. In some embodiments, the airway sensor may be a gas exchange detector to generate an airway pattern or a gas exchange pattern in a respiratory cycle. The gas exchange pattern may be displayed to a user of the intubation device. The trachea opening is identified based on the gas exchange features of the gas exchange pattern.

Further, it should be appreciated that the intubation device may include a data processor configured to analyze the airway data to determine an airway pattern indicating a trachea opening based on airway features. In some embodiments, the airway data may be analyzed via pattern matching by comparing the airway features of the image data with a predetermined pattern as described above. In some embodiments, the airway data may be analyzed via pattern recognition as described above. Further, as described above, a navigation element may be generated to direct a movement of the guide stylet to the trachea opening.

Figure 16:
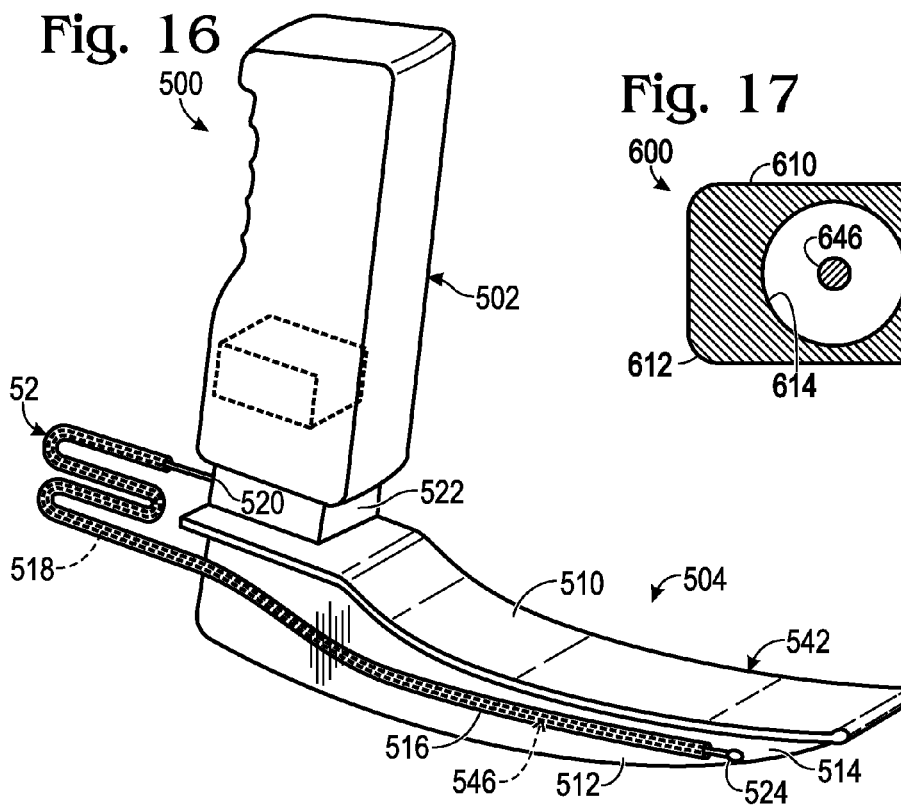
FIG. 16 is a perspective view of an example intubation device according to another embodiment of the present disclosure.

FIG. 16 shows an example intubation device 500 according to another embodiment of the present disclosure. Intubation device 500 includes an insertion guide device 502 and a blade assembly 504. Insertion guide device 504 may include electronic components for identification of a trachea opening or a trachea. Blade assembly 504 includes a blade 542 and a guide stylet 546. Similar to the embodiment illustrated in FIG. 15, blade assembly 502 is configured to have an in-line alignment of the guide stylet 546 and an ETT 52. In the depicted embodiment, blade 542 includes a press plate 510 and a side plate 512. Press plate 510 has a surface curved along a length of the blade and the length is sized to allow a distal end 514 of the blade to be positioned adjacent to the trachea opening once the blade is inserted into a patient's mouth. Press plate 510 may depress a patient's tongue to allow a view of the trachea opening or the vocal cords. Side plate 512 extends from a surface of press plate 510 and is substantially perpendicular to press plate 510. Side plate 512 may constrain ETT 52 to move along the surface of press plate 510. Again, blade 542 may have any appropriate shape.

Guide stylet 546 may include a first section 516 to be disposed along a length of blade 542 and a second section 518. Second section 518 may be in a folded configuration, where one or more segments are folded on a top or below substantially one or more other segments. For example, in some embodiments, the folded configuration may include a stagger configuration, an L-shaped configuration, an S-shaped configuration, a spiral configuration, a helical configuration. In some embodiments, the guide stylet may be made of rigid materials, such as metal or hard plastics so that the guide stylet may be rigidly suspended over blade 542 or suspended substantially stationary while the guide stylet is fixed at one mounting portion 520 or one point at a connection block 522 of the blade assembly. In some embodiments, guide stylet 546 may be connected to connection block 522 by any appropriate connection mechanism, such as welding at mounting portion 520. Blade assembly 504 may be releasably connected to insertion guide device 502. Guide stylet 546 is coupled with insertion guide device 502 mechanically, electronically or optically.

As guide stylet 546 is suspected all the way from a distal end 514 to mounting portion 518, ETT 52 can be loaded from distal end 514 of the blade to second section 518 of the guide stylet. That is, the ETT 52 can be moved over the guide stylet. Further, a precision light guide may be disposed on a tip of guide stylet to direct the ETT's movement.

As described above with reference to FIG. 15, a trachea identifying device may be disposed on a tip 524 of guide stylet 546 to identify the trachea opening. It should be appreciated that any appropriate trachea identifying device can be used. For example, the trachea identifying device may be an airway sensor, such as a light source, an image capture device, a gas exchange detector, a sound detector or a light detector as described above. The trachea opening can be identified based on information from the image capture device or the gas exchange detector. In one example, an airway pattern may be used to identify the trachea opening as described above. Further, it should be appreciated that the guide stylet may be flexible.

Intubation device 500 has advantage of in-line arrangement of the guide stylet and the ETT. Further, as one section of the guide stylet is folded and the ETT can be loaded along the folded segments of the guide stylet, the blade assembly is compact.

Figure 17:
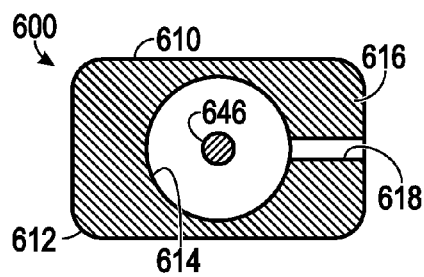
FIG. 17 shows a cross-sectional view of a blade assembly according to another embodiment of the present disclosure.

FIG. 17 shows a cross-sectional view of a blade assembly 600 according to another embodiment of the present disclosure. Blade assembly 600 may have an in-line alignment as described above with reference to FIGS. 15 and 16. Blade 642 may be formed of a tube configuration. Outside surfaces 610 of blade 642 is of a rectangular shape with round corners 612 and inside surfaces 614 of blade 642 is circular to accommodate an insertion of the ETT. Blade 642 may be curved along its length to facilitate positioning into a patient's mouth.

Guide stylet 646 is shown to be substantially in middle portion of blade 642. Guide stylet may be sized to receive a trachea identifying device. Guide stylet 642 may be rigid and fixed to a blade assembly or an intubation device as described above with reference to FIGS. 15 and 16. While guide stylet is shown to have a circular configuration, it can be any appropriate shape.

In the depicted embodiment, a side wall 616 of blade 646 includes a passage 618 to accommodate an ETT balloon and accessories for after-intubation use. Side wall 616 may also include one or more slots (not shown) so that a user can observe a movement of ETT as ETT is pushed into the trachea.

According to one aspect of the present disclosure, a blade assembly of an intubation system comprises a blade having a distal end wherein the distal end is adjacent to a trachea opening when the blade is inserted into an upper airway of a patient; and a guide stylet suspended along a portion of the blade and extended along the blade. An ETT can be loaded from a distal end of the blade into the guide stylet. In one embodiment, the guide stylet is rigidly fixed to the intubation system and unmovable.

In another embodiment, the guide stylet is moveable by a drive mechanism to perform one ore multiple degrees freedom movements. The blade can be functioned as a guide rail to facilitate movement forward and backward of the guide stylet along an insertion direction and the distal end of the blade is a fulcrum for the movement of the guide stylet in at least one degrees of freedom. In still another embodiment, the intubation system further comprises a guide stylet locking solenoid to couple the guide stylet with the drive mechanism and an endotracheal tube locking solenoid to couple the endotracheal tube with an endotracheal tube shuttle to enable movement of the endotracheal tube by the endotracheal tube shuttle.

Note that various steps or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated steps or functions may be repeatedly performed depending on the particular strategy being used. Further, the described steps may graphically represent code to be programmed into the computer readable storage medium in guide control device.

Note that various steps or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated steps or functions may be repeatedly performed depending on the particular strategy being used. Further, the described steps may graphically represent code to be programmed into the computer readable storage medium in guide control device.

The invention claimed is:

1. An intubation system, comprising:
a moveable guide stylet to be inserted into an upper airway of a patient to guide insertion of an endotracheal tube into a patient's trachea;
at least one trachea identifying device positioned on the guide stylet to detect airway data as the guide stylet moves in the upper airway; and
an insertion guide device including:
a data processor configured to analyze the airway data to determine an airway pattern indicating a position of the guide stylet relative to a trachea opening based on airway features, and generate a navigation element to direct a movement of the guide stylet to the trachea opening.

2. The intubation system of claim 1, wherein the trachea identifying device is an image capture device, the airway pattern is a topographical pattern and the airway features are topographical features, wherein the topographical features include one of an inverted V shape of vocal cords, white color of the vocal cords, vocal cord folds vibration, thermal image changes during a respiratory cycle, a vocal cord's spatial relationship to an epiglottis, a glottis, and arytenoids, wherein the navigation element directs the guide stylet toward the trachea opening and prevents the guide stylet from entering an esophagus opening.

3. The intubation system of claim 1, the trachea identifying device is an image capture device, the airway pattern is a topographic pattern that is determined based on topographical features, wherein the image capture device includes a thermal camera to capture thermal image data wherein the topographical features include thermal image color variations of vocal cords and a vocal cord opening due to temperature changes in a respiratory cycle of the patient.

4. The intubation system of claim 2, wherein the insertion guide device further includes a display device to display image data, the topographical pattern, the navigation element, and the position of the guide stylet, or a movement of the guide stylet in real time.

5. The intubation system of claim 1, wherein the trachea identifying device is a gas exchange detector to detect dynamic gas exchange data during a respiratory cycle of the patient, the airway pattern is a gas exchange pattern and the airway features are gas exchange features wherein the gas exchange features include variations of a gas exchange variable during the respiratory cycle.

6. The intubation system of claim 5, wherein the gas exchange variable is one of air flow, pressure, CO2 concentration, O2 concentration, temperature, and humidity, and the gas exchange detector is an airflow sensor, a pressure sensor, a CO2 sensor, an O2 sensor, a temperature sensor, and a humidity sensor to detect variations of air flow, pressure, CO2 concentration, O2 concentration, temperature, and humidity, respectively during one of inhalation and exhalation of the respiratory cycle.

7. The intubation system of claim 1, wherein the airway data is analyzed via pattern matching by comparing the airway features of the image data with a predetermined pattern.

8. The intubation system of claim 1, wherein the airway data is analyzed via pattern recognition.

9. The intubation system of claim 1, wherein the insertion guide device further includes a display device to display the navigation element, and the guide stylet is moved manually by a user of the intubation system based on the navigation element with one degree of freedom of movement or at least two degrees of freedom of movement.

10. The intubation system of claim 1, further comprising a blade configured to have a length such that a distal end of the blade is adjacent to the trachea opening when the blade is placed into a patient's mouth, wherein the guide stylet is suspended along the length of the blade and the endotracheal tube is preloaded into the guide stylet from the distal end of the blade and is capable of moving along the guide stylet toward the trachea opening.

11. The intubation system of claim 10, further comprising a precision light guide disposed on the guide stylet to generate a light ray pointing toward a direction of movement of the guide stylet such that the endotracheal tube is moved into the trachea following the light ray.

12. An intubation system, comprising:
a blade including a distal end, the distal end adjacent to a trachea opening when the blade is inserted into an upper airway of a patient;
a guide stylet disposed in the blade and moveable along the blade to guide insertion of an endotracheal tube into a patient's trachea;
at least one trachea identifying device positioned on the guide stylet to detect airway data as the guide stylet moves in the upper airway; and
an insertion guide device including:
a data processor configured to analyze the airway data to determine an airway pattern indicating a position of the guide stylet relative to the trachea opening based on airway features, and to generate a navigation element to direct a movement of the guide stylet to the trachea opening,
a display device to display the navigation element,
a drive mechanism to move the guide stylet with three degrees of freedom, and
an actuator configured to actuate the drive mechanism via a user of the intubation system.

13. The intubation system of claim 12, wherein the trachea identifying device is one of an image capture device to capture image data and a gas exchange detector to detect gas exchange data, the airway features are one of topographical features and gas exchange features, and the airway pattern is one of a topographical pattern and a gas exchange pattern.

14. The intubation system of claim 13, wherein the guide stylet includes a tip portion and a body, wherein a first degree of freedom of movement of the guide stylet is the tip portion of the guide stylet moving up and down relative to a length of the guide stylet, a second degree of freedom of movement of the guide stylet is the tip portion of the guide stylet moving left and right relative to the length of the guide stylet, and a third degree of freedom of movement of the guide stylet is the body of the guide stylet moving forward and backward.

15. The intubation system of claim 14, where the third degree of freedom is caused by a leadscrew mechanism, a roller mechanism, or a telescoping mechanism, and the first degree of freedom is caused by a first motor, and the second degree of freedom is caused by a second motor.

16. The intubation system of claim 15, further comprising a precision light guide disposed on the guide stylet to generate a light ray pointing toward a direction of the movement of the guide stylet such that the endotracheal tube is moved into the trachea following the light ray.

17. An intubation device, comprising:
a blade having a blade body and a distal end, where the distal end is positioned adjacent to a patient's trachea opening when the blade is inserted into a patient's mouth;

a guide stylet having a tip adjacent to the distal end and an endotracheal tube loading section extending from a mounting portion of the guide stylet toward the blade, where the guide stylet is fixed on the mounting portion and suspended along a length of the blade such that an endotracheal tube is preloaded into the endotracheal tube loading section before an intubation; and a trachea identifying device disposed on the tip of the guide stylet to sense airway data and generate an airway pattern viewable by a user for identification of the trachea opening.

18. The intubation device of claim 17, wherein the guide stylet is suspended substantially at a fixed position and the mounting portion is on the blade or another component of the intubation device.

19. The intubation device of claim 17, wherein the trachea identifying device is one of a light source, a gas exchange detector, a sound detector and a light detector.

20. The intubation device of claim 17, further include a precision light guide to guide an insertion of the endotracheal tube into the trachea opening and the endotracheal tube loading section is in a folded configuration.

* * * * *